(12) United States Patent
Ra et al.

(10) Patent No.: US 11,788,061 B2
(45) Date of Patent: Oct. 17, 2023

(54) METHOD FOR PRODUCING MESENCHYMAL STEM CELLS THAT INHIBIT PROLIFERATION OF CANCER CELLS

(71) Applicant: Jeong Chan Ra, Chungcheongbuk-do (KR)

(72) Inventors: Jeong Chan Ra, Chungcheongbuk-do (KR); Eun-Young Kim, Seoul (KR)

(73) Assignee: Jeong Chan Ra, Chungcheongbuk-Do (KR)

( * ) Notice: Subject to any disclaimer, the term of this patent is extended or adjusted under 35 U.S.C. 154(b) by 579 days.

(21) Appl. No.: 16/321,520

(22) PCT Filed: Jul. 28, 2017

(86) PCT No.: PCT/KR2017/008176
§ 371 (c)(1),
(2) Date: Feb. 27, 2019

(87) PCT Pub. No.: WO2018/021879
PCT Pub. Date: Feb. 1, 2018

(65) Prior Publication Data
US 2020/0010805 A1    Jan. 9, 2020

(30) Foreign Application Priority Data

Jul. 29, 2016 (KR) .......................... 10-2016-0097107

(51) Int. Cl.
*C12N 5/0775* (2010.01)
*A61K 35/28* (2015.01)

(52) U.S. Cl.
CPC ............ *C12N 5/0662* (2013.01); *A61K 35/28* (2013.01); *C12N 5/0663* (2013.01); *C12N 5/0665* (2013.01); *C12N 5/0667* (2013.01); *C12N 5/0668* (2013.01); *C12N 2500/14* (2013.01); *C12N 2500/30* (2013.01); *C12N 2500/38* (2013.01); *C12N 2501/11* (2013.01); *C12N 2501/33* (2013.01); *C12N 2501/39* (2013.01)

(58) Field of Classification Search
CPC .. C12N 5/0662; C12N 5/0668; C12N 5/0663; C12N 5/0665; C12N 5/0667; C12N 2500/14; C12N 2500/30; C12N 2500/38; C12N 2501/11; C12N 2501/33; C12N 2501/39
See application file for complete search history.

(56) References Cited

U.S. PATENT DOCUMENTS

| | | | | |
|---|---|---|---|---|
| 2012/0263685 | A1* | 10/2012 | Ra | A61P 35/00 514/8.4 |
| 2015/0118194 | A1 | 4/2015 | Ra et al. | |
| 2015/0118748 | A1 | 4/2015 | Ra et al. | |
| 2016/0206660 | A1* | 7/2016 | Shi | C12N 5/0662 |

FOREIGN PATENT DOCUMENTS

| | | | | |
|---|---|---|---|---|
| CN | 104520423 A | 4/2015 | | |
| CN | 104603263 A | 5/2015 | | |
| CN | 105132369 A | 12/2015 | | |
| CN | 105530946 A | 4/2016 | | |
| JP | 2015514416 A | 5/2015 | | |
| JP | 201552607 A | 9/2015 | | |
| JP | 2015526067 A | 9/2015 | | |
| JP | 2016519142 A | 6/2016 | | |
| KR | 1020100114170 A | 10/2010 | | |
| KR | 1020140125943 A | 10/2014 | | |
| KR | 1020130117343 A | * 10/2015 | ............. | C12N 5/074 |
| WO | 2011070974 A1 | 6/2011 | | |

OTHER PUBLICATIONS

Tang et al., Aspirin treatment improved mesenchymal stem cell immunomodulatory properties via the 15d-PGJ2/PPARγ/TGF-β1 pathway. Stem Cells Development, vol. 23, No. 17 (2014) pp. 2093-2103. (Year: 2014).*

Cao, Y., et al., "Aspirin promotes bone marrow mesenchymal stem cell-based calvarial bone regeneration in mini swine", "Stem Cell Research & Therapy", 2015, Page(s) doi: 10.1186/s13287-015-0200-4, vol. 6, No. 1, Publisher: BioMed Central.

Du, M., et al., "Lower dosage of aspirin promotes cell growth and osteogenic differentiation in murine bone marrow stromal cells", "Journal of Dental Sciences", 2016, pp. 315-322;, vol. 11, No. 3, Publisher: Science Direct.

Kidd, S., et al., "Mesenchymal stromal cells alone or expressing interfron—suppress pancreatic tumors in vivo, an effect countered by anti-inflammatory treatment", "Cytotherapy", 2010, pp. 615-625 doi:10.3109/1465324100363815, vol. 12, No. 5, Publisher: Informa healthcare.

Orendi, M. et al., "Effects of vitamins C and E, acetylsalicylic acid and heparin on fusion, beta-hCG and PP13 expression in BeWo cells", "Placenta", 2010, pp. 431-438, vol. 31, No. 5, Publisher: Elsevier.

Tang, J., et al., "Aspirin Treatment Improved Mesenchymal Stem Cell Immunomodulatory Properties via the 15d-PGJ2/PPAR/TGF-1 Pathway", "Stem Cells and Development", 2014, pp. 2093-2103; doi:10.1089/scd.2014.0081, vol. 23, No. 17, Publisher: Mary Ann Liebert, Inc.

(Continued)

*Primary Examiner* — Kara D Johnson
(74) *Attorney, Agent, or Firm* — HULTQUIST, PLLC; Steven J. Hultquist

(57) ABSTRACT

Disclosed are a medium composition for culturing mesenchymal stem cells for the treatment of cancer which can inhibit proliferation of cancer cells, while maintaining differentiation capability and activity thereof, and a method for producing mesenchymal stem cells for the treatment of cancer using the composition. More particularly, disclosed are a medium composition containing vitamin C and aspirin for producing mesenchymal stem cells having improved inhibitory activity against proliferation of cancer cells, and a method for producing mesenchymal stem cells for the treatment of cancer using the composition.

9 Claims, 14 Drawing Sheets
(14 of 14 Drawing Sheet(s) Filed in Color)
Specification includes a Sequence Listing.

(56) References Cited

OTHER PUBLICATIONS

Atsuta, I., et al., "Mesenchymal Stem Cells Inhibit Multiple Myeloma Cells Via the Fas/Fas Ligand Pathway", "Stem Cell Research & Therapy", 2013, pp. 2-14, vol. 4, No. 111.

Bharadwaj, S., et al., "Multipotential Differentiation of Human Urine-Derived Stem Cells: Potential for Therapeutic Applications in Urology", "Stem Cells", 2013, pp. 1840-1856, vol. 31, No. 9.

Funes, J., et al., "Oncogenic Transformation of Mesenchymal Stem Cells Decreases Nrf2 Expression Favoring In Vivo Tumor Growth and Poorer Survival", "Molecular Cancer", 2014, pp. 1-17, vol. 13, No. 20.

Guan, J., et al., "Biological Characteristics of Human-Urine-Derived Stem Cells: Potential for Cell-Based Therapy in Neurology", "Tissue Engineering", 2014, pp. 1794-1806, vol. 20, Nos. 13 and 14.

Hsieh, C., et al., "Aspirin Breaks the Crosstalk Between 3T3-L1 Adipocytes and 4T1 Breast Cancer Cells by Regulating Cytokine Production", "PLOS One", Jan. 21, 2016, pp. 1-17, vol. 11, No. 1.

Lin, H., et al., "Knockdown of OCT4 Suppresses the Growth and Invasion of Pancreatic Cancer Cells Through Inhibition of the AKT Pathway", "Molecular Medicine Reports", 2014, pp. 1335-1342, vol. 9.

Wong, R., "Mesenchymal Stem Cells: Angels or Demons?", "Journal of Biomedicine and Biotechnology", 2011, pp. 1-8, vol. 2011.

Zhang, D., et al., "Urine-Derived Stem Cells: A Novel and Versatile Progenitor Source for Cell-Based Therapy and Regenerative Medicine", "Genes & Diseases", 2014, pp. 8-17, vol. 1.

Zhang, Y., et al., "Aspirin Counteracts Cancer Stem Cell Features, Desmoplasia and Gemcitabine Resistance in Pancreatic Cancer", "Oncotarget", Feb. 5, 2015, pp. 9999-10015, vol. 6, No. 12.

Text of First Office Action in CN201780058891.8, dated Jul. 5, 2022.

Text of Search Report in Chinese Patent Application No. 201780058891.8, dated Jun. 15, 2022.

Basu, T.K., "Vitamin C-aspirin interactions", Int. J. Vitam. Nutr. Res. Suppl., 1982, vol. 23, pp. 83-90, Abstract, https://pubmed.ncbi.nlm.nih.gov/68114490/.

Chen C., et al., "Telomerase governs immunology properties of mesenchymal stem cells by regulating FAS ligand expression", EMBO Molecular Medicine, 2014, pp. 322-334, vol. 6, No. 3.

Yamaza, T., et al., "Pharmacologic Stem Cell Based Intervention as a New Approach to Osteoporosis Treatment in Rodents", Pios ONE, 2008, pp. e2615; doi:10.137/journal.pone.0002615, vol. 3, No. 7.

\* cited by examiner n=7,*p<0.05,p<0.01,*p<0.001

A. VEGF Gel photo

B. VEGF Gene level(revers transcription - PCR)

SEQUENCE LISTING

<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: hTRAIL-F

<400> SEQUENCE: 1
atggctatga tggaggtcca gg          22

<210> SEQ ID NO 2
<211> LENGTH: 23
<212> TYPE: DNA
<213> ORGANISM: Artificial Sequence
<220> FEATURE:
<223> OTHER INFORMATION: hTRAIL-R

<400> SEQUENCE: 2
tcagctcgtt ggtaaagtac acg          23

```
<210> SEQ ID NO 3
<211> LENGTH: 20
<212> TYPE: DNA
<213> ORGANISM: Artificial Sequence
<220> FEATURE:
<223> OTHER INFORMATION: h Fas L-F

<400> SEQUENCE: 3
ctggggatgt ttcagctctt                                               20

<210> SEQ ID NO 4
<211> LENGTH: 21
<212> TYPE: DNA
<213> ORGANISM: Artificial Sequence
<220> FEATURE:
<223> OTHER INFORMATION: h Fas L-R

<400> SEQUENCE: 4
gtggcctatt tgcttctcca a                                             21

<210> SEQ ID NO 5
<211> LENGTH: 19
<212> TYPE: DNA
<213> ORGANISM: Artificial Sequence
<220> FEATURE:
<223> OTHER INFORMATION: h CXCR4-F

<400> SEQUENCE: 5
gcggaaaacc aagacgctc                                                19

<210> SEQ ID NO 6
<211> LENGTH: 20
<212> TYPE: DNA
<213> ORGANISM: Artificial Sequence
<220> FEATURE:
<223> OTHER INFORMATION: h CXCR4-R

<400> SEQUENCE: 6
ttcatgtgcg cgtaactgtc                                               20

<210> SEQ ID NO 7
<211> LENGTH: 20
<212> TYPE: DNA
<213> ORGANISM: Artificial Sequence
<220> FEATURE:
<223> OTHER INFORMATION: h VEGF-A-F

<400> SEQUENCE: 7
tgagcttcct acagcacaac                                               20

<210> SEQ ID NO 8
<211> LENGTH: 21
<212> TYPE: DNA
<213> ORGANISM: Artificial Sequence
<220> FEATURE:
<223> OTHER INFORMATION: h VEGF-A-R

<400> SEQUENCE: 8
gaacgctcca ggacttatac c                                             21

<210> SEQ ID NO 9
<211> LENGTH: 20
<212> TYPE: DNA
<213> ORGANISM: Artificial Sequence
<220> FEATURE:
```

```
<223> OTHER INFORMATION: h Nrf2-F

<400> SEQUENCE: 9
accagtggat ctgccaacta                                              20

<210> SEQ ID NO 10
<211> LENGTH: 20
<212> TYPE: DNA
<213> ORGANISM: Artificial Sequence
<220> FEATURE:
<223> OTHER INFORMATION: h Nrf2-R

<400> SEQUENCE: 10
acgtagccga agaaacctca                                              20

<210> SEQ ID NO 11
<211> LENGTH: 20
<212> TYPE: DNA
<213> ORGANISM: Artificial Sequence
<220> FEATURE:
<223> OTHER INFORMATION: h c-Myc-F

<400> SEQUENCE: 11
aaggccccca aggtagttat                                              20

<210> SEQ ID NO 12
<211> LENGTH: 20
<212> TYPE: DNA
<213> ORGANISM: Artificial Sequence
<220> FEATURE:
<223> OTHER INFORMATION: h c-Myc-R

<400> SEQUENCE: 12
ttccgcaaca agtcctcttc                                              20

<210> SEQ ID NO 13
<211> LENGTH: 20
<212> TYPE: DNA
<213> ORGANISM: Artificial Sequence
<220> FEATURE:
<223> OTHER INFORMATION: h p21-F

<400> SEQUENCE: 13
tgtcttgtac ccttgtgcct                                              20

<210> SEQ ID NO 14
<211> LENGTH: 21
<212> TYPE: DNA
<213> ORGANISM: Artificial Sequence
<220> FEATURE:
<223> OTHER INFORMATION: h p21-R

<400> SEQUENCE: 14
gcgtttggag tggtagaaat c                                            21

<210> SEQ ID NO 15
<211> LENGTH: 19
<212> TYPE: DNA
<213> ORGANISM: Artificial Sequence
<220> FEATURE:
<223> OTHER INFORMATION: h Sox2-F

<400> SEQUENCE: 15
gcggaaaacc aagacgctc                                               19
```

```
<210> SEQ ID NO 16
<211> LENGTH: 20
<212> TYPE: DNA
<213> ORGANISM: Artificial Sequence
<220> FEATURE:
<223> OTHER INFORMATION: h Sox2-R

<400> SEQUENCE: 16
ttcatgtgcg cgtaactgtc                                              20

<210> SEQ ID NO 17
<211> LENGTH: 21
<212> TYPE: DNA
<213> ORGANISM: Artificial Sequence
<220> FEATURE:
<223> OTHER INFORMATION: h Nanog-F

<400> SEQUENCE: 17
tccaacatcc rcaacctcag c                                            21

<210> SEQ ID NO 18
<211> LENGTH: 20
<212> TYPE: DNA
<213> ORGANISM: Artificial Sequence
<220> FEATURE:
<223> OTHER INFORMATION: h Nanog-R

<400> SEQUENCE: 18
ccttctgcgt cacaccattg                                              20

<210> SEQ ID NO 19
<211> LENGTH: 20
<212> TYPE: DNA
<213> ORGANISM: Artificial Sequence
<220> FEATURE:
<223> OTHER INFORMATION: h Oct4-F

<400> SEQUENCE: 19
cactgtactc ggtcccttc                                               20

<210> SEQ ID NO 20
<211> LENGTH: 21
<212> TYPE: DNA
<213> ORGANISM: Artificial Sequence
<220> FEATURE:
<223> OTHER INFORMATION: h Oct4-R

<400> SEQUENCE: 20
caggcacctc agtttgaatg c                                            21

<210> SEQ ID NO 21
<211> LENGTH: 25
<212> TYPE: DNA
<213> ORGANISM: Artificial Sequence
<220> FEATURE:
<223> OTHER INFORMATION: h Bcl2-F

<400> SEQUENCE: 21
gggtacgata accgggagat agtga                                        25

<210> SEQ ID NO 22
<211> LENGTH: 20
<212> TYPE: DNA
<213> ORGANISM: Artificial Sequence
<220> FEATURE:
<223> OTHER INFORMATION: h Bcl2-R
```

```
<400> SEQUENCE: 22
ggaggagaag atgcccggtg                                                20

<210> SEQ ID NO 23
<211> LENGTH: 20
<212> TYPE: DNA
<213> ORGANISM: Artificial Sequence
<220> FEATURE:
<223> OTHER INFORMATION: h PPAR-r-F

<400> SEQUENCE: 23
ttagatgaca gcgacttggc                                                20

<210> SEQ ID NO 24
<211> LENGTH: 20
<212> TYPE: DNA
<213> ORGANISM: Artificial Sequence
<220> FEATURE:
<223> OTHER INFORMATION: h PPAR-r-R

<400> SEQUENCE: 24
ggcttgtagc aggttgtctt                                                20

<210> SEQ ID NO 25
<211> LENGTH: 22
<212> TYPE: DNA
<213> ORGANISM: Artificial Sequence
<220> FEATURE:
<223> OTHER INFORMATION: h Apaf 1-F

<400> SEQUENCE: 25
cttcttccag tgtaaggaca gt                                             22

<210> SEQ ID NO 26
<211> LENGTH: 20
<212> TYPE: DNA
<213> ORGANISM: Artificial Sequence
<220> FEATURE:
<223> OTHER INFORMATION: h Apaf 1-R

<400> SEQUENCE: 26
cagcctgcca ttccatgtat                                                20
```

METHOD FOR PRODUCING MESENCHYMAL STEM CELLS THAT INHIBIT PROLIFERATION OF CANCER CELLS

CROSS-REFERENCE TO RELATED APPLICATIONS

This application is a U.S. national phase under the provisions of 35 U.S.C. § 371 of International Patent Application No. PCT/KR17/08176 filed Jul. 28, 2017, which in turn claims priority of Korean Patent Application No. 10-2016-0097107 filed Jul. 29, 2016. The disclosures of such International Patent Application No. PCT/KR17/08176 and Korean Patent Application No. 10-2016-0097107 are hereby incorporated herein by reference in their respective entireties, for all purposes.

TECHNICAL FIELD

The present invention relates to a medium composition for culturing mesenchymal stem cells for treating cancer which can inhibit proliferation of manufacture cancer cells, while maintaining activity thereof. More particularly, the present invention relates to a medium composition containing vitamin C and aspirin for producing mesenchymal stem cells having improved inhibitory activity against proliferation of cancer cells.

BACKGROUND ART

Stem cells refer to cells that are capable of self-replicating and differentiating into two or more cells. Stem cells are classified into totipotent stem cells, pluripotent stem cells and multipotent stem cells.

Totipotent stem cells refer to omnipotent cells that can develop into one perfect individual and embryonic cells up to the eight-cell stage after fertilization of an egg with a sperm have these properties. When these cells are isolated and transplanted into the uterus, they can develop into one perfect individual.

Pluripotent stem cells refer to cells that are capable of developing into various cells and tissues derived from the ectoderm, mesoderm and endoderm and may be derived from an inner cell mass located inside blastocysts generated 4-5 days after fertilization. Such cells are called "embryonic stem cells" and can differentiate into various other tissue cells, but not form new living organisms.

Multipotent stem cells refer to stem cells that are only capable of differentiating into cells specific to tissues and organs containing these cells. Multipotent stem cells are involved in the growth and development of tissues and organs of the fetal, neonatal and adult stages, as well as in maintenance of homeostasis of adult tissues and functions of inducing regeneration of damaged tissue. Tissue-specific multipotent cells are collectively referred to as "mesenchymal stem cells".

Mesenchymal stem cells (Rebecca SY Wong, et al., *J Biomed Biotechnol* 24: 2011, 2011) have been used in cell-based therapies in a variety of disease conditions such as heart disease, osteogenesis imperfecta and spinal cord injury, and the results are in the spotlight. In addition, recent studies had been made on cell-based therapies and regenerative medicine using urine-derived stem cells (Bharadwaj et al., *Stem Cells.* 31 (9): 1840-56, 2013; Zhang D et al., *Genes Dis.* 1): 8-17, 2014; Guan et al., *Tissue Eng,* 20 (13-14): 1794-806, 2014).

However, some studies have reported side effects of MSC treatment. In particular, several studies have shown that MSCs cause rapid tumor growth and metastasis by tumor mutations and malignant mutations and is resistant to anticancer drugs. In addition, various studies have shown spontaneous malignant transformation of mesenchymal stem cells.

Meanwhile, "cancer" is characterized by "uncontrolled cell growth", and such abnormal cell growth causes formation of a mass of cells called a "tumor", that penetrates into the surrounding tissues and, in severe cases, may metastasize into other organs, which is also called academically "neoplasia".

Methods for treating cancer include surgery, radiotherapy, chemotherapy including administering anticancer drugs and the like. Anticancer drugs are drugs that act on cancer cells proliferating indefinitely to inhibit the proliferation and growth of the cancer cells. Alkylating anticancer drugs such as cisplatin and cyclophosphamide, which are widely used at present, covalently bind to nitrogen in nucleotides constituting DNA and thus exhibit anticancer activity. 5-fluorouracil inhibits enzymes involved in biosynthesis of nucleic acids, or is directly inserted into DNA or RNA and thus becomes active.

In addition, antibiotics such as adriamycin act strongly on DNA to inhibit the inherent functions of DNA, and thus exhibit anticancer effects. However, these anticancer drugs act not only on tumor cells but also on normal cells, in particular, rapidly proliferating and differentiating living cells such as bone marrow cells or intestinal epithelial cells, and thus are accompanied by various side effects such as nephrotoxicity, vomiting and neurotoxicity.

In addition, cancer stem cells in tumors remain in a resting stage unlike other cancer cells and are less aggressive than metastatic cancer cells. Therefore, such cells survive, excluded from attacks of the anticancer drugs, such that the tumor cannot be completely removed only by inducing the death (apoptosis) of common cancer cells present in the tumor.

Accordingly, as a result of intensive efforts to develop therapeutic agents for cancer using mesenchymal stem cells to overcome side effects of anticancer drugs and the like, the present inventors have found that mesenchymal stem cells produced by culture in a medium supplemented with aspirin, vitamin C and the like have the effects of inhibiting the proliferation of cancer cells, while maintaining the activity of the cells, thus completing the present invention.

DISCLOSURE

Technical Problem

Therefore, it is an object of the present invention to provide a medium composition comprising vitamin C and aspirin for producing mesenchymal stem cells that has improved inhibitory activity against the proliferation of cancer cells, and a method for producing mesenchymal stem cells having improved inhibitory activity against the proliferation of cancer cells by culturing the mesenchymal stem cells in the medium.

Technical Solution

In accordance with the present invention, the above and other objects can be accomplished by the provision of a medium composition for producing mesenchymal stem cells, that contains aspirin and has improved inhibitory activity against proliferation of cancer cells.

In accordance with another aspect of the present invention, provided is a method for producing mesenchymal stem cells with improved ability to inhibit proliferation of cancer cells, including culturing the mesenchymal stem cells in a medium containing aspirin.

In accordance with another aspect of the present invention, provided is use of a medium composition containing aspirin for producing mesenchymal stem cells, for the production of mesenchymal stem cells with improved ability to inhibit proliferation of cancer cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

DETAILED DESCRIPTION OF THE INVENTION

Figure 1:
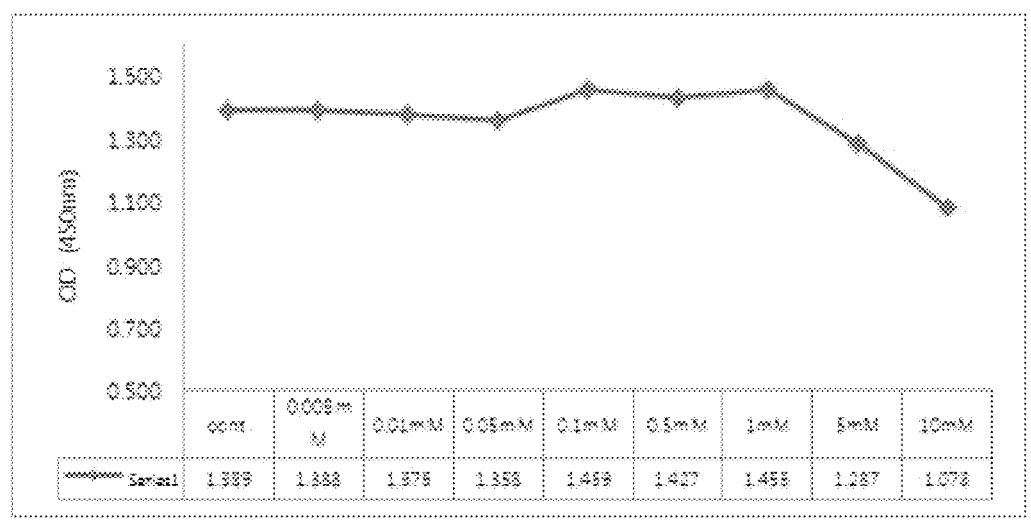
FIG. 1 shows a result of analysis of cytotoxicity of Vit.C-MSCs depending on aspirin concentration.

Unless defined otherwise, all technical and scientific terms used herein have the same meaning as appreciated by those skilled in the field to which the present invention pertains. In general, nomenclature used herein is well-known in the art and is ordinarily used.

Adult stem cells refer to stem cells that are known to have a multipotent ability to differentiate into only the tissues and organ-specific cells in the stage at which embryogenesis occurs to form embryonic organs, or the adult stage. Multipotent stem cells having a tissue-specific differentiation ability are stem cells that can only differentiate into cells specific to the tissues and organs containing the cells, which are involved in the growth and development of respective tissues and organs in the fetal stage, neonatal stage and adult stage, as well as the maintenance of homeostasis of adult tissues and the function to induce regeneration of damaged tissues.

In the present invention, adult stem cells, preferably human-derived adult stem cells, are used.

Such adult stem cells may be derived from tissues such as adipose, uterus, bone marrow, muscles, placenta, umbilical cord blood, urine or skin (epithelium). Preferably, adult stem cells obtained from adipose tissues, or epithelial tissues such as hair follicles and amnion tissues can be used. In particular, mesenchymal stem cells (MSCs) are preferably used and human adipose tissue-derived mesenchymal stem cells (AT-MSCs) are the most preferably used.

The urine-derived stem cells according to the present invention have self-renewal and multipotent abilities, and express mesenchymal stem cell markers. That is, the urine-derived stem cells can differentiate into mesodermal cell lines such as endothelial cells, osteogenic cells, chondrocytes, adipocytes and skeletal muscle cells, and endodermal cell lines such as urothelial cells. In addition, urine-derived stem cells are known to have high telomerase activity and long telomeres (Bharadwaj et al, *Stem Cells.* 31(9):1840-56, 2013; Stem Cells: Current Challenges and New Directions Part of the series Stem Cell Biology and Regenerative Medicine, 19-28: 2013).

As used herein, the term "stem cells" refers to cells that are capable of self-replicating and differentiating into two or more cells, and the term "adult stem cells" refers to stem cells in the stage at which embryogenesis occurs to form embryonic organs, or the adult stage.

As used herein, the term "mesenchymal stem cells" refers to undifferentiated stem cells isolated from human or mammalian tissues, which may be derived from various tissues. In particular, mesenchymal stem cells may be umbilical cord-derived mesenchymal stem cells, umbilical cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amnion-derived mesenchymal stem cells and placenta-derived mesenchymal stem cells, and methods for isolating stem cells from respective tissues are well-known in the art.

As used herein, the term "adipose-derived mesenchymal stem cells" refers to undifferentiated stem cells isolated from adipose tissues and the isolation method thereof can be, for example, as follows. More particularly, after culturing a fat-containing suspension floating in physiological saline obtained by liposuction, the stem cell layer adhered to the culture container such as a flask is treated with trypsin and then collected, or the substance suspended in a small amount of physiological saline is directly collected by scrapping, to isolate the adipose-derived mesenchymal stem cells.

Such "adipose tissue-derived adult stem cells" or "adipose tissue-derived mesenchymal stem cells" are undifferentiated adult stem cells isolated from adipose tissue and are abbreviated herein as "adipose stem cells". Such cells can be obtained through conventional methods well-known in the art.

As the medium used for obtaining the adipose stem cell product, a conventional medium known to be suitable for stem cell culture can be used. Preferably, DMEM (Dulbecco's modified Eagle medium) or keratinocyte-SFM (keratinocyte serum free medium) may be used, and a mixture of IMDM (Iscove's Modified Dulbecco's Medium), a-MEM (alpha modification of Eagle's medium), F12 (nutrient mixture F-12) and DMEM/F12 (Dulbecco's modified eagle medium: nutrient mixture F-12) may be used, but the present invention is not limited thereto.

The medium for culturing adipose stem cells can be supplemented with an additive that inhibits differentiation while promoting the proliferation of undifferentiated phenotypes of adipose stem cells. In addition, the medium may generally contain a neutral buffer (e.g., phosphate and/or high-concentration bicarbonate) and a protein nutrient (e.g., serum, such as FBS, serum substitutes, albumin or an essential amino acid and a nonessential amino acid such as glutamine). Furthermore, the medium may contain lipid (fatty acid, cholesterol, serum HDL or LDL extracts) and other ingredients found in this type of most preservative media (such as insulin or transferrin, nucleoside or nucleotide, pyruvate, sugar sources in the form of any ionized or salts such as glucose, selenium, glucocorticoids such as hydrocortisone and/or reducing agents such as β-mercaptoethanol).

In addition, preferably, the medium also contains anti-clumping agents such as products sold by Invitrogen (Cat #0010057AE) in order to prevent cells from adhering to each other, adhering to the container wall, or forming too large bundles.

In particular, the medium for obtaining or culturing adipose stem cells used in one embodiment of the present invention preferably contains a basic medium selected from the group consisting of DMEM, defined Keratinocyte-SFM, alpha-MEM, IMDM, F12 and DMEM/F12, as well as a medium composition for culturing mesenchymal stem cells that contains L-ascorbic acid 2-phosphate (vitamin C), fetal bovine serum and N-acetyl-L-cysteine and is further supplemented with aspirin, but the present invention is not limited thereto.

In the present invention, the medium may contain 0.05 to 1 mM ascorbic acid 2-phosphate, 2 to 20% fetal bovine serum, 0.2 to 20 mM N-acetyl-L-cysteine, and 0.1 to 1 mM aspirin, but the present invention is not limited thereto.

In one aspect, the present invention is directed to a medium composition for producing mesenchymal stem cells, that contains aspirin and has improved inhibitory activity against proliferation of cancer cells.

In another aspect, the present invention is directed to a method for producing mesenchymal stem cells with improved ability to inhibit proliferation of cancer cells, including culturing the mesenchymal stem cells in a medium containing aspirin.

In another aspect, the present invention is directed to use of a medium composition containing aspirin for producing mesenchymal stem cells, for the production of mesenchymal stem cells with improved ability to inhibit proliferation of cancer cells.

In the present invention, the medium preferably further contains vitamin C, but the present invention is not limited thereto.

In the present invention, the medium is preferably DMEM or K-SFM containing 5 to 10% FBS and NAC (N-acetyl cysteine), more preferably, further contains calcium, rEGF, insulin and hydrocortisone, but the present invention is not limited thereto.

In the present invention, the mesenchymal stem cells are preferably pretreated with vitamin C, but the present invention is not limited thereto.

In the present invention, the mesenchymal stem cells are preferably derived from tissues selected from the group consisting of adipose, uterus, bone marrow, muscle, placenta, umbilical cord blood, urine, hair follicle and skin, but the present invention is not limited thereto.

In the present invention, the concentration of the aspirin is preferably 0.1 mM to 1 mM, but the present invention is not limited thereto.

In the present invention, the culture time is preferably 24 hours, but the present invention is not limited thereto.

In the present invention, the cancer cells are preferably glioma, gliosarcoma, anaplastic astrocytoma, medulloblastoma, lung cancer, small cell lung cancer, cervical carcinoma, colon cancer, rectal cancer, chordoma, throat cancer, Kaposi's sarcoma, lymphatic sarcoma, lymphatic endothelial sarcoma, colorectal cancer, endometrial cancer, ovarian cancer, leukemia, prostate cancer, kidney cell carcinoma, liver carcinoma, cholangiocarcinoma, choriocarcinoma, seminoma, testicular tumor, Wilm's tumor, Ewing's tumor, bladder carcinoma, angiosarcoma, endothelial sarcoma, adenocarcinoma, hidradenoma, sebaceous carcinoma, papillary carcinoma, papillary sarcoma, cystic sarcoma, bronchial carcinoma, medullary carcinoma, mast cell tumor, mesothelioma, synovioma, melanoma, leiomyoma, rhabdomyoma, neuroblastoma, retinoblastoma, oligodendroglioma, acoustic neuroma, hemangioblastoma, meningioma, pinealoma, ependymoma, craniopharyngioma, epithelial carcinoma, embryonal carcinoma, squamous cell carcinoma, basal cell carcinoma, fibrosarcoma, myxoma, mucosal sarcoma, liposarcoma, chondrosarcoma, osteogenic sarcoma or cancer stem cells, more preferably, breast or pancreatic cancer cells, but the present invention is not limited thereto.

In another aspect, the present invention is directed to a method of treating cancer including administering mesenchymal stem cells with improved ability to inhibit proliferation of cancer cells, produced by culturing mesenchymal stem cells in a medium containing aspirin.

In another aspect, the present invention is directed to the use of mesenchymal stem cells with improved inhibitory activity against proliferation of cancer cells, produced by culturing mesenchymal stem cells in a medium containing aspirin, for the treatment of cancer.

"Cancer" is characterized by uncontrolled cell growth. Such abnormal cell growth causes formation of a mass of cells called "tumor" that penetrates into surrounding tissues and, in severe cases, metastasizes into other organs.

The term "anti-cancer" is intended to encompass not only the treatment of a cancer disease, that is, inhibition of proliferation of cancer cells or cancer stem cells, or elimination of cancer cells or cancer stem cells, but also prevention of a cancer disease, that is, improvement of resistance to cancer prior to the onset of cancer. Thus, the term "prevention or treatment of cancer" or "inhibition of proliferation of cancer" and "anti-cancer" are used herein interchangeably.

In the present invention, the term "cancer cells" includes cells that undergo abnormal cell growth due to genetic variation (mutation) in proliferation and growth mechanisms of normal cells and have an aggressive mobility to other organs, which may be referred to as "metastasis". In addition, cancer stem cells are known to be present in tumors and are considered to be caused by abnormal transfer of genetic information from normal stem cells. Cancer stem cells are maintained and proliferate due to the presence of the microenvironment called "niche" for survival thereof, the presence of niche, and the surrounding normal cells, immune-related cells or differentiated cancer cells are known to affect the maintenance of characteristics and proliferation thereof.

The term "therapeutic", as herein used, unless otherwise indicated, refers to reversing, palliating, inhibiting or preventing the disease or disorder to which the term applies, or one or more symptoms of the disease or disorder.

As used herein, the term "treatment" refers to an action of treatment when the term "therapeutic" is defined as above. Thus, the "treatment" or "therapy" of cancer in mammals includes one or more of the following:

(1) inhibiting growth of cancer, i.e., suppressing development thereof, (2) preventing the diffusion of cancer, i.e., preventing metastasis, (3) alleviating cancer, i.e., causing regression of cancer, (4) preventing recurrence of cancer, and (5) palliating symptoms of cancer.

Cancer is an intractable chronic disease that cannot be fundamentally treated in many cases even through treatment with surgery, radiotherapy and chemotherapy, causes severe pain to patients and ultimately leads to death. Over the past several decades, surgery, chemotherapy (treatment with anti-cancer drugs), radiotherapy and the like have been greatly advanced, but failed to provide ultimate solutions to cancer.

There are contradictory reports associated with effects of stem cells as cancer therapeutic agents on inhibition or promotion of cancer. It could be seen from the present invention that such opposite (contradictory) effects vary depending on medium and method for culturing stem cells.

In one embodiment of the present invention, mesenchymal stem cells with improved inhibitory activity against proliferation of cancer cells are produced by culturing adipose-derived mesenchymal stem cells cultured in a vitamin C-containing medium in an aspirin-containing medium. In other words, the mesenchymal stem cells according to the present invention may be stem cells having an anticancer function which are produced by culturing adipose-derived mesenchymal stem cells cultured through pre-treatment with vitamin C in a medium containing aspirin, and may be stem cells having an anticancer function which are produced by culturing adipose-derived mesenchymal stem cells in a medium containing both vitamin C and aspirin, and may be stem cells which are produced by culturing adipose-derived mesenchymal stem cells cultured through pre-treatment with vitamin C in a medium containing both vitamin C and aspirin. The present inventors called all of these stem cells "Angel stem cells".

EXAMPLE

Hereinafter, the present invention will be described in more detail with reference to examples. However, it is obvious to those skilled in the art that these examples are provided only for illustration of the present invention and should not be construed as limiting the scope of the present invention.

EXAMPLE

Example 1: Isolation of Human Adipose Tissue-Derived Mesenchymal Stem Cells

Human adipose tissues obtained from abdominal fat were isolated by liposuction and washed with PBS. The tissues were minced and digested using DMEM supplemented with collagenase type 1 (1 mg/ml) for 2 hours at 37° C. The tissues were washed with PBS and then centrifuged at 1,000 rpm for 5 minutes. The supernatant was suctioned and the pellet remaining on the bottom was washed with PBS and then centrifuged at 1,000 rpm for 5 minutes. The debris was removed by filtration through a 100 μm mesh, washed with PBS, and then cultured in a DMEM medium containing 10% FBS, 2 mM NAC, and 0.2 mM ascorbic acid.

After allowing to stand overnight, unattached cells were washed with PBS and sub-cultured while replacing RKCM-N medium, that is, a keratinocyte-SFM medium (containing 5% FBS, 2 mM NAC, 0.2 mM ascorbic acid, 0.09 mM calcium, 5 ng/ml rEGF, 5 μg/ml insulin and 74 ng/ml hydrocortisone) every 2 days to isolate adipose tissue-derived multipotent mesenchymal stem cells.

The adipose tissue-derived multipotent mesenchymal stem cells thus obtained were Vit.C-MSCs cultured in a medium containing vitamin C, that is, MSCs pre-treated with vitamin C, which were used in the following examples.

The origins of various media and reagents used in the following examples are shown in Table 1 below.

TABLE 1

| Ingredients | Origin |
| --- | --- |
| Ascorbic acid | Sigma |
| CaCl$_2$ | Sigma |
| Collagenase type I | Gibco |
| DMEM (Dulbecco's modified Eagle medium) | Gibco |
| DPBS (Dulbecco's Phosphate-Buffered Salines) | Welgene |
| EGF (Epidermal growth factor) | Gibco |
| FBS (Fetal Bovine Serum) | Gibco |
| Hydrocortisone | Sigma |
| Insulin | Gibco |
| K-SFM (Keratinocyte-SFM) | Gibco |
| NAC (N-acetyl Cysteine) | Sigma |

Example 2: Evaluation of Toxicity of Aspirin on Vit.C-MSCs

The Vit.C-MSCs cultured in a medium containing vitamin C of Example 1 were seeded on a 96-well cell culture plate at a concentration of $1 \times 10^4$ cells/plate, and then incubated overnight for cell adherence and stabilization. Then, the cells were cultured in a fresh RKCM-N medium, that is, keratinocyte-SFM containing 5% FBS, 2 mM NAC, 0.2 mM ascorbic acid, 0.09 mM calcium, 5 ng/ml rEGF, 5 μg/ml insulin and 74 ng/ml hydrocortisone, supplemented with aspirin in various concentrations of 0.005 mM, 0.001 mM, 0.05 mM, 0.1 mM, 0.5 mM, 1 mM, 5 mM and 10 mM, for 24 hours. A cck-8 (cell counting Kit-8, Dojindo) solution (10 μl/100 μl) was added to each well and reacted for 2 hours, and the absorbance at 450 nm was measured using a plate reader (Lonza).

As a result, it could be seen from FIG. 1 that there was almost no cytotoxicity of Vit.C-MSCs at an aspirin concentration of 5 mM or less. Thus, in the following analysis, aspirin was used in a concentration of 0.1 to 1 mM.

Example 3: Characteristics of Vit.C-MSCs Cultured in Aspirin-Containing Medium The Vit.C-MSCs cultured in a medium containing vitamin C of Example 1 were incubated for 2 days for adherence and stabilization. Then, the Vit.C-MSCs were cultured in fresh RKCM-N medium supplemented with concentrations of 0.1 mM, 0.5 mM, 1 mM and 10 mM of aspirin for 24 hours.

Figure 2:
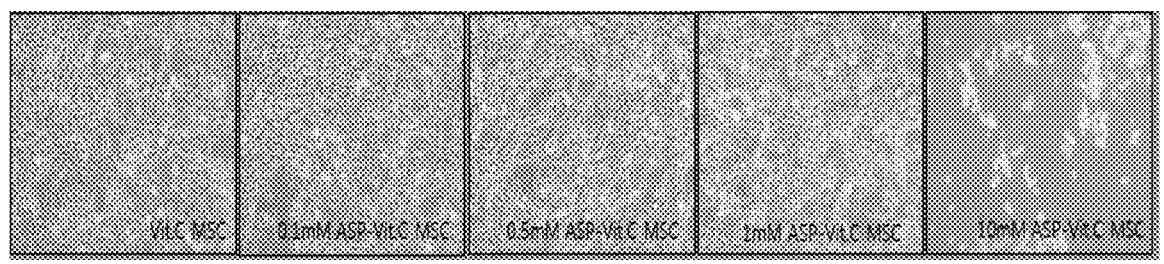
FIG. 2 shows the morphology of Vit.C-MSCs cultured in an aspirin-containing medium.
Figure 3:
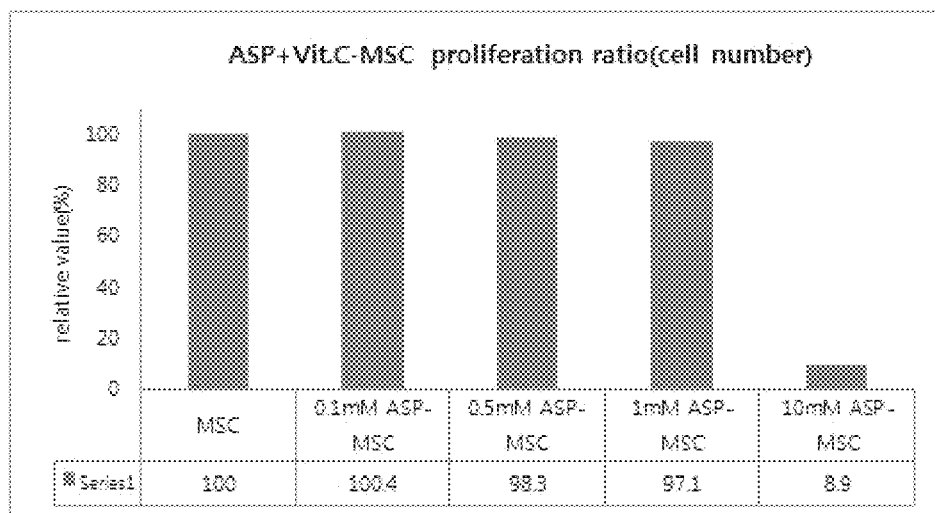
FIG. 3 shows the proliferation rate, viability and cell size of Vit.C-MSCs cultured in an aspirin-containing medium.
Figure 3:
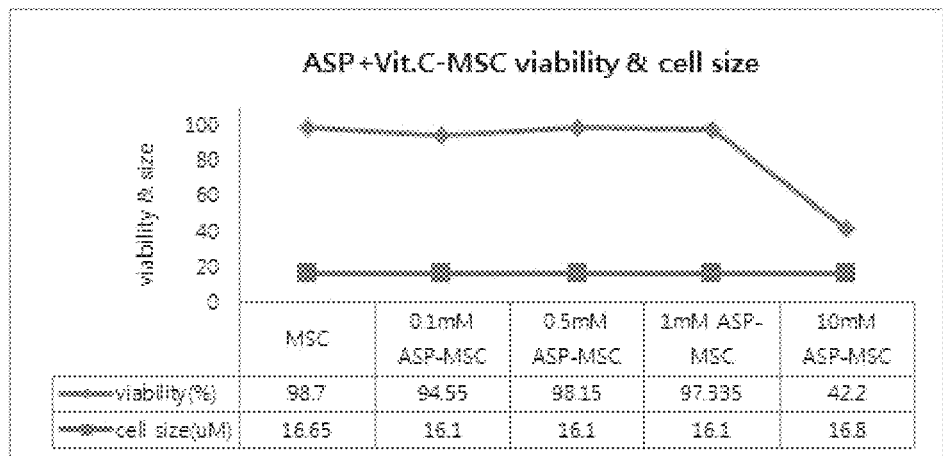

The cell morphologies of Vit.C-MSCs by aspirin were monitored with an electron microscope (100× magnification, Leica DMIL) (FIG. 2), and the proliferation rate, viability and cell size were analyzed using a Luna automated cell counter (Logoy) (FIG. 3).

As a result, it was confirmed that the aspirin concentration of 1 mM or less did not affect the morphology, proliferation rate, viability and cell size of stem cells (FIGS. 2 and 3).

Example 4: Analysis of Stemness (Stem Cell Capability) of Vit.C-MSCs Cultured in Aspirin-Containing Medium 4-1: CFA (Colony Forming Assay)

The Vit.C-MSCs cultured in a medium containing vitamin C were cultured for 2 days for adherence and stabilization, and were then cultured in fresh RKCM-N media supplemented with aspirin at concentrations of 0.1 mM, 0.5 mM and 1 mM for 24 hours. Then, 300 cells for each aspirin concentration were mixed with an RKCM-N medium and seeded on a 100 mm cell culture dish. While the culture medium was changed every 2 to 3 days, the cells were cultured at 37° C. and 5% $CO_2$ for 10 days. After 10 days, the medium was removed, and 3 ml of 0.1% crystal violet reagent was added thereto, followed by reaction for 10 minutes, followed by washing and drying. The number of colonies formed was counted and colony formation ability (plating efficiency, PE) was calculated by the equation of "number of colonies/total number of cells seeded×100%".

Figure 4:
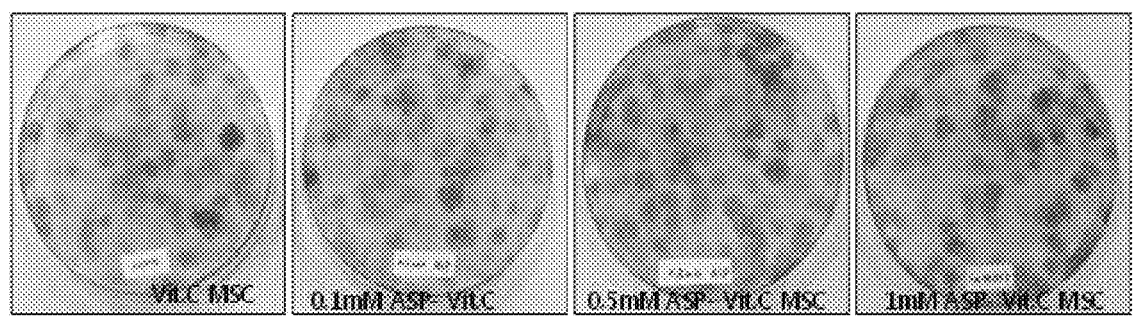
FIG. 4 is an image showing a result of colony forming assay (CFA) of Vit.C-MSCs cultured in an aspirin-containing medium.
Figure 5:
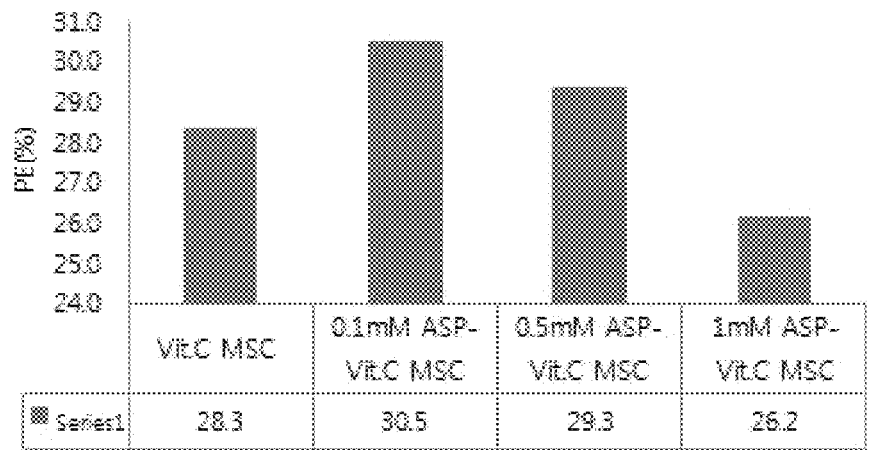
FIG. 5 shows a result of measurement of colony forming assay (CFA) of Vit.C-MSCs cultured in an aspirin-containing medium.
Figure 6:
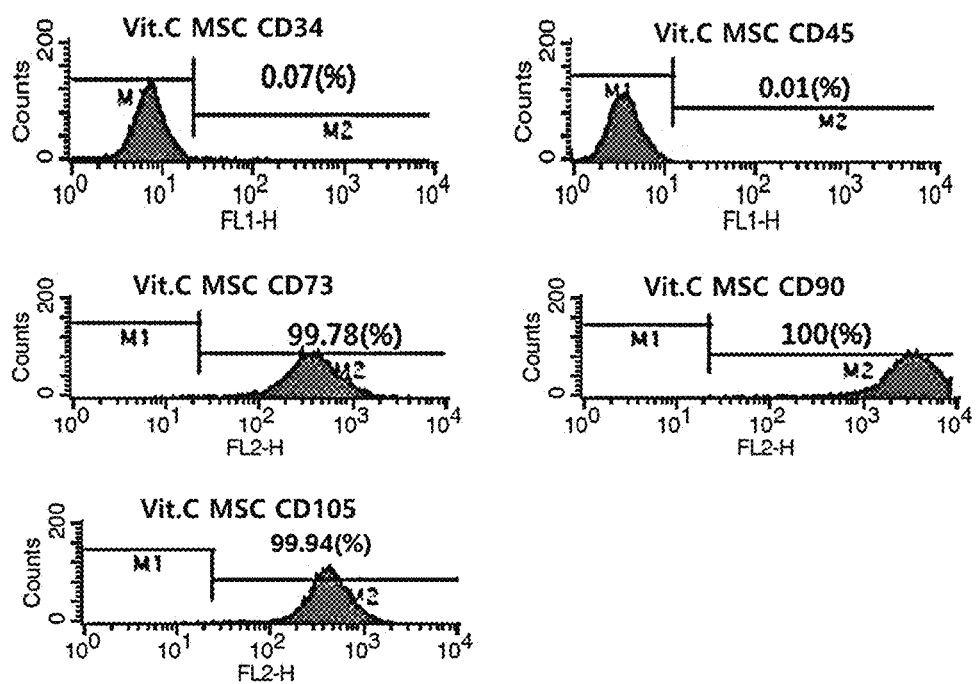
FIG. 6 shows a result of FACS to analyze CD marker expression of Vit.C-MSCs cultured in a control medium containing no aspirin.
Figure 7:
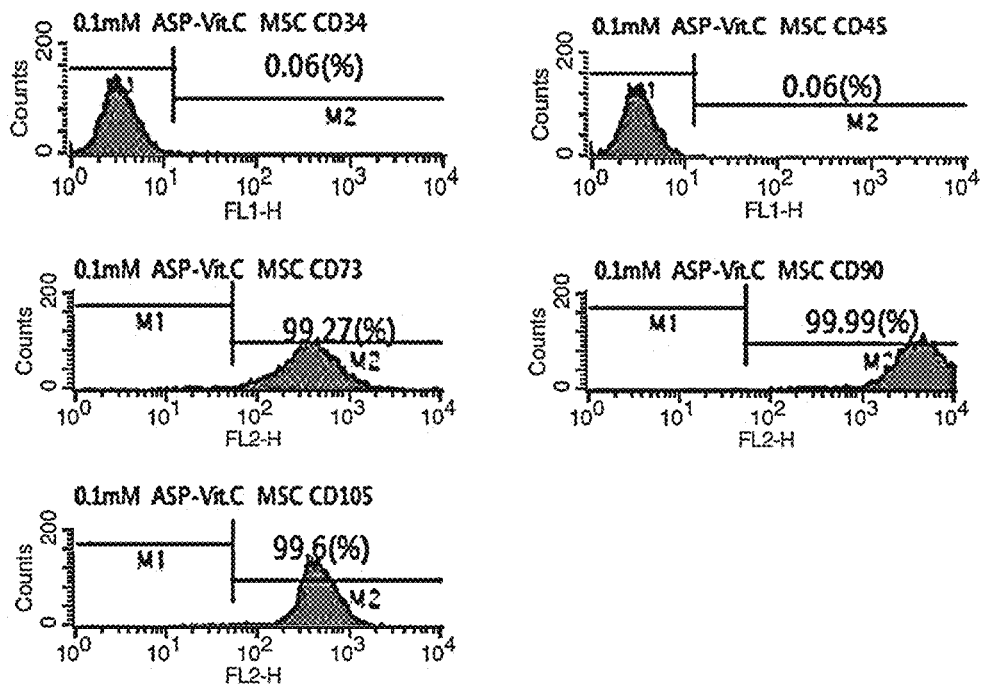
FIG. 7 shows a result of FACS to analyze CD marker expression of Vit.C-MSCs cultured in a 0.1 mM aspirin-containing medium.
Figure 8:
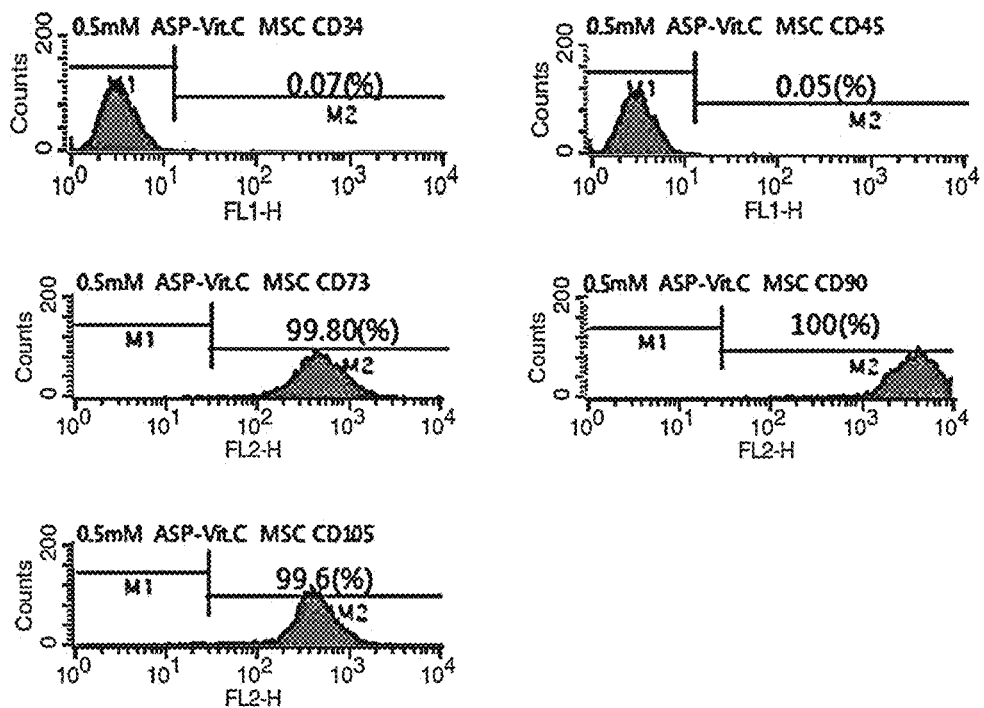
FIG. 8 shows a result of FACS to analyze CD marker expression of Vit.C-MSCs cultured in a 0.5 mM aspirin-containing medium.
Figure 9:
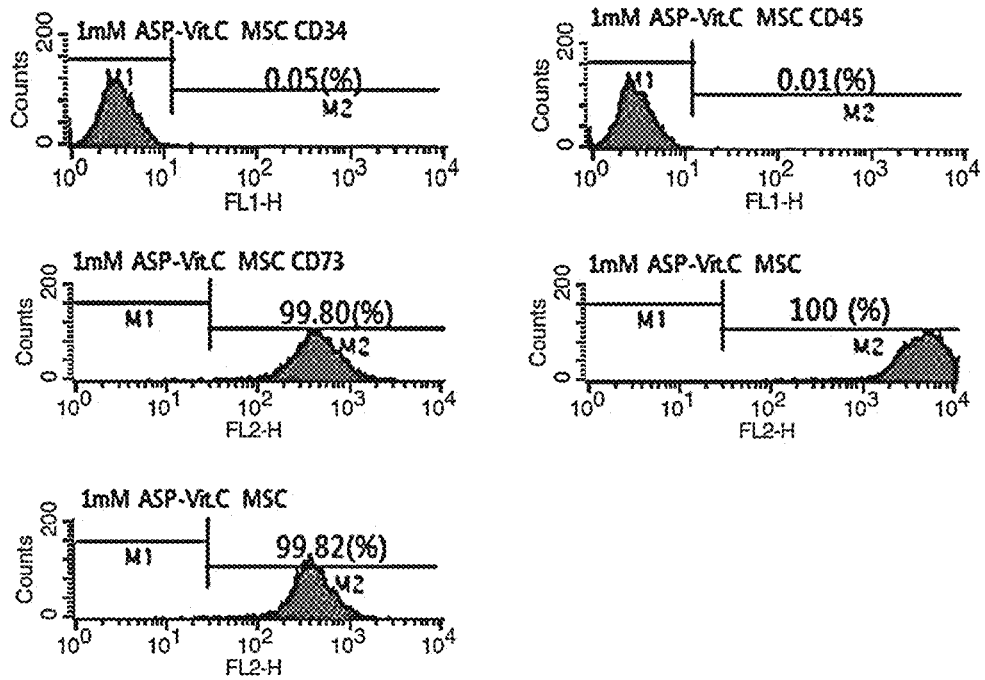
FIG. 9 shows a result of FACS to analyze CD marker expression of Vit.C-MSCs cultured in a 1 mM aspirin-containing medium.

As a result, the Vit.C-MSCs cultured in a medium containing aspirin at a concentration of 1 mM or less showed no change in colony forming ability and thus stem cells neither lost stemness nor changed stem cell capabilities (FIGS. 4 and 5).

4-2: Identification of Surface CD Markers

The Vit.C-MSCs cultured in a medium containing vitamin C were cultured for 2 days for adherence and stabilization, and were cultured in fresh RKCM-N media supplemented with aspirin at concentrations of 0.1 mM, 0.5 mM and 1 mM for 24 hours.

The CD marker expression on the stem cell surface in the following Table 2 was compared between two types of MSCs, that is, Vit.C-MSCs and ASP-Vit.C-MSCs cultured in aspirin using FACS.

TABLE 2

| Marker | Vit. C MSC (%) | 0.1 mM ASP-Vit. C MSC (%) | 0.5 mM ASP-Vit. C MSC (%) | 1 mM ASP-Vit. C MSC (%) |
| --- | --- | --- | --- | --- |
| CD34 | 0.03 | 0.12 | 0.01 | 0.01 |
| CD45 | 0.00 | 0.02 | 0.02 | 0.00 |

TABLE 2-continued

| Marker | Vit. C MSC (%) | 0.1 mM ASP-Vit. C MSC (%) | 0.5 mM ASP-Vit. C MSC (%) | 1 mM ASP-Vit. C MSC (%) |
|---|---|---|---|---|
| CD73 | 99.92 | 99.93 | 99.98 | 99.72 |
| CD90 | 100 | 100 | 100 | 100 |
| CD105 | 99.97 | 99.96 | 99.99 | 99.85 |

As a result, as can be seen from FIGS. 6 to 9, the CD marker expression on the stem cell surface was not changed depending on 0.1 mM, 0.5 mM and 1 mM of aspirin. That is, the Vit.C-MSCs cultured in an aspirin-containing medium neither lost stemness (characteristics of stem cells) nor changed stem cell capabilities.

Example 5: Identification of Differentiation Ability of Vit.C-MSCs Cultured in Aspirin-Containing Medium 5-1: Induction of Adipocyte Differentiation The Vit.C-MSCs cultured in a medium containing vitamin C were cultured for 2 days for adherence and stabilization, and were then cultured in fresh RKCM-N media supplemented with aspirin at concentrations of 0.1 mM, 0.5 mM and 1 mM for 24 hours. Then, the cells were seeded at $2\times10^4$ cells on a 12-well plate and cultured for 14 days while replacing the medium every 2 to 3 days with a STEMPRO adipogenesis differentiation kit.

Figure 10:
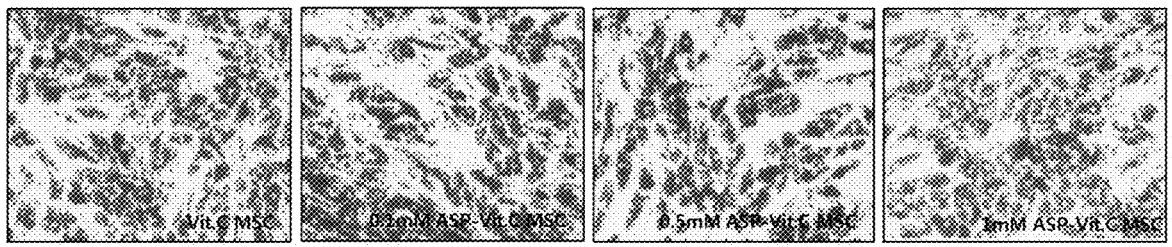
FIG. 10 shows a result of Oil Red 0 staining to identify the ability of Vit.C-MSCs cultured in an aspirin-containing medium to differentiate into adipocytes.
Figure 11:
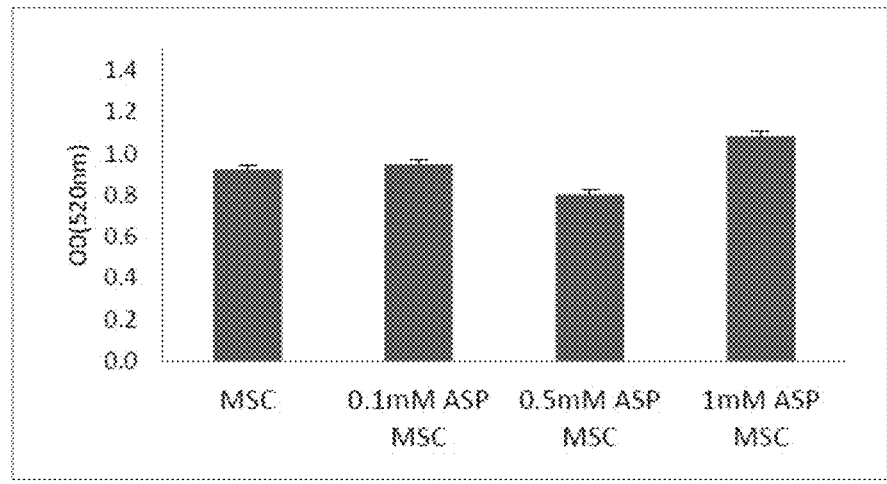
FIG. 11 shows a result of measurement of absorbance at 520 nm to identify a differentiation level of Vit.C-MSCs cultured in an aspirin-containing medium into adipocytes.

After differentiation of induction for 14 days, the cells were stained with Oil Red O and analyzed with a microscope. As a result, differentiation into adipocytes was identified (FIG. 10). The Oil Red O-stained cells were destained with isopropanol to identify the degree of differentiation from absorbance at 520 nm (FIG. 11).

5-2: Induction of Osteocyte Differentiation

The Vit.C-MSCs cultured in a medium containing vitamin C were cultured for 2 days for adherence and stabilization, and were then cultured in fresh RKCM-N media supplemented with aspirin at concentrations of 0.1 mM, 0.5 mM and 1 mM for 24 hours. Then, $2\times10^4$ cells were seeded on a 12-well plate and cultured for 21 days while replacing the medium every 2 to 3 days with a STEMPRO adipogenesis differentiation kit.

Figure 12:
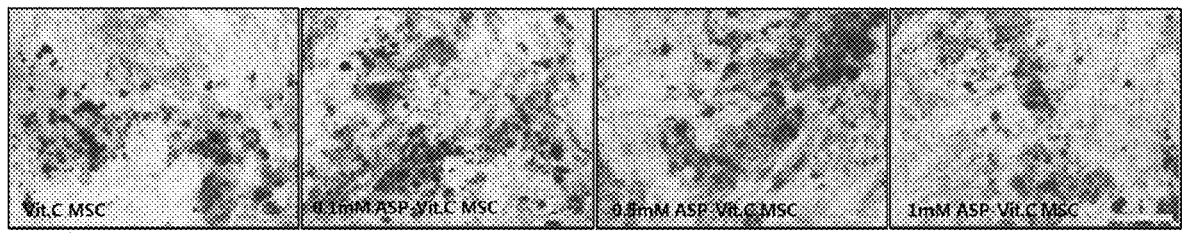
FIG. 12 shows a result of Alizarin Red S staining to identify the ability of Vit.C-MSCs cultured in an aspirin-containing medium to differentiate into osteocytes.
Figure 13:
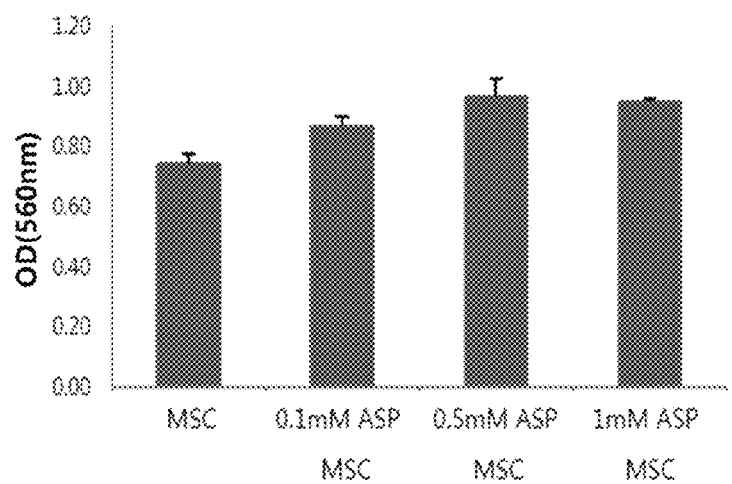
FIG. 13 shows a result of measurement of absorbance at 560 nm to identify a differentiation level of Vit.C-MSCs cultured in an aspirin-containing medium into osteocytes.

After differentiation induction for 21 days, the cells were stained with Alizarin Red S and analyzed with a microscope. As a result, differentiation into osteocytes was identified (FIG. 12). The Alizarin Red-stained cells were destained with 10% cetylpyridinium chloride to identify the degree of differentiation from absorbance at 560 nm (FIG. 13).

Example 6: Identification of Anticancer Effects by Direct Co-Culture of Vit.C-MSCs Cultured in Aspirin-Containing Medium with Cancer Cells 6-1: Breast Cancer and Pancreatic Cancer Cells In order to conduct direct co-culture, the Vit.C-MSCs cultured in a medium containing vitamin C of Example 1 were inoculated at a confluence (density) of 10% ($0.5\times10^6$ cells) with RKCM-N medium in a T75 flask. After 2 days, when the confluence reached 50 to 60%, an RKCM-N medium, that is, a keratinocyte-SFM medium containing 5% FBS, 2 mM NAC, 0.2 mM ascorbic acid, 0.09 mM calcium, 5 ng/ml rEGF, 5 µg/ml insulin and 74 ng/ml hydrocortisone was treated with aspirin at concentrations of 0.5 mM, 1 mM and 10 mM, and cultured for 24 hours and then ASP-Vit.C-MSC (Angel-stem cells) were then collected.

Figure 20:
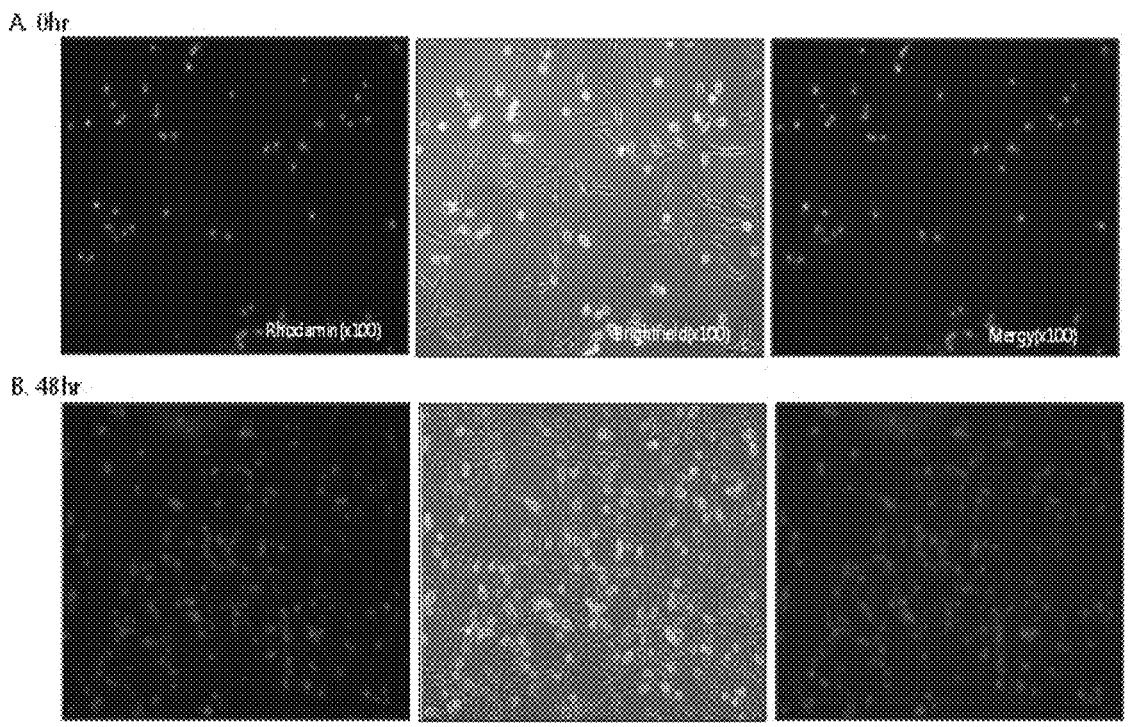
FIG. 20 is a fluorescence microscopic image at 0 hours and 48 hours after direct culture of Vit.C-MSCs cultured in a 0.5 mM aspirin-containing medium with PANC-1 cancer cells (red) in a cancer cell culture medium.

Then, $2\times10^7$ breast cancer cells (MCF-7) and $2\times10^7$ pancreatic cancer cells (PANC-1) were washed twice with serum-free DMEM medium, respectively. The cells were stained for 10 min with 4 µl of a red staining solution per 1 ml of a diluent C solution using a PKH26 red fluorescent cell linker kit (Sigma). The cells were blocked for 1 minute with the same volume of serum (FBS), washed twice with a DMEM medium supplemented with serum and reacted in a medium supplemented with serum (FBS) for 30 minutes. The stained cancer cells were identified with a fluorescence microscope (100× magnification, ZEISS, Mirax) (FIG. 20). MCF-7 and PANC-1 cancer cells fluorescently labeled with red fluorescent dye were seeded at a density of $0.5\times10^5$ cells/dish on a 100 mm cell culture dish, and allowed to attach and stabilize overnight.

In order to identify the anticancer effect by direct co-culture of the ASP-Vit.C-MSCs and cancer cells, $0.5\times10^6$ ASP-Vit.C-MSC cells were further seeded on 100-mm cell culture dishes, to which the MCF-7 and PANC-1 cancer cells were attached, respectively. The total number of cells including cancer cells and stem cells was adjusted to $1\times10^6$, cells were cultured for 48 hours in DMEM medium containing 10% FBS, and all the cells were then collected. The cell number, viability and cell size of the collected cells were identified using a Luna automated cell counter (Logoy), and the distribution of fluorescently stained cancer cells with regard to the collected cells was identified with FACS.

As a result, the distribution of the fluorescently stained cancer cells was significantly lower in ASP-Vit.C-MSCs having an aspirin concentration of 0.5 mM than in Vit.C-MSCs in both breast cancer cells (MCF-7) and pancreatic cancer cells (PANC-1). That is, the anticancer effect of Angel-stem cells was excellent (FIGS. 14 to 16).

Figure 14:
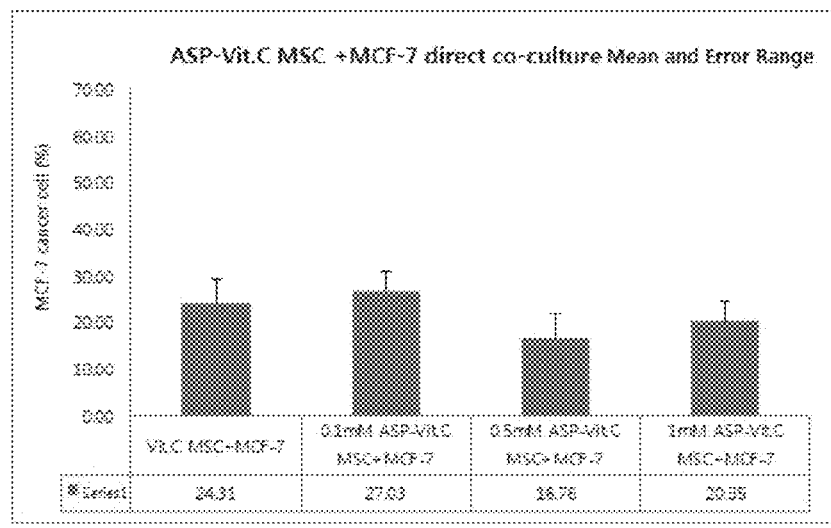
FIG. 14 shows a result of calculation of a ratio of cancer cell number to total cell number, after direct co-culture of Vit.C-MSCs cultured in an aspirin-containing medium with MCF-7 cancer cells in a cancer cell culture medium, followed by determination of the distribution of the cancer cells by FACS.
Figure 15:
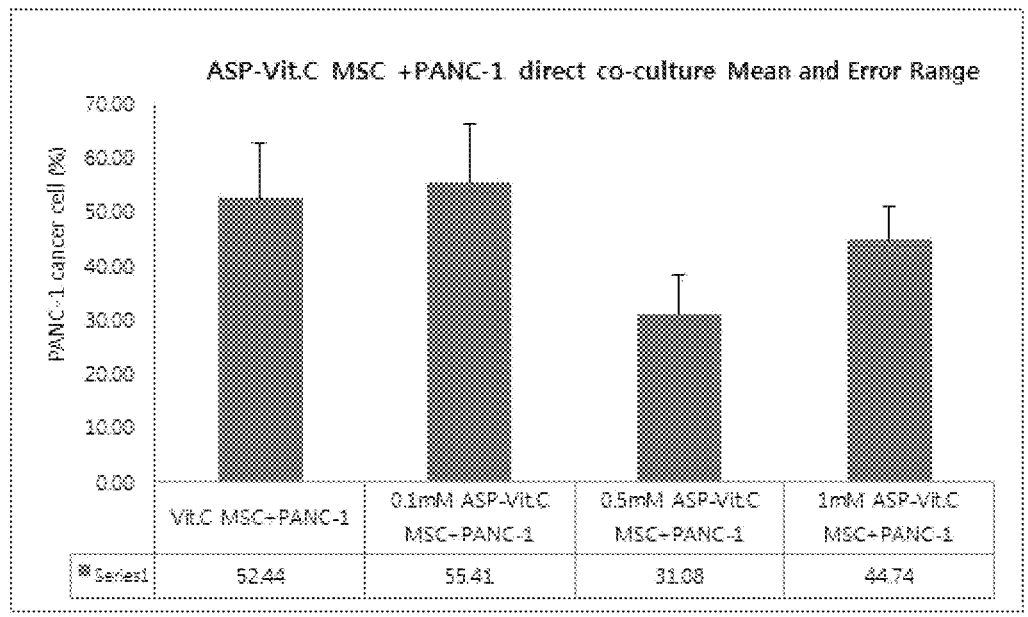
FIG. 15 shows a result of calculation of a ratio of cancer cell number to total cell number, after direct co-culture of Vit.C-MSCs cultured in an aspirin-containing medium with PANC-1 cancer cells in a cancer cell culture medium, followed by determination of the distribution of the cancer cells by FACS.
Figure 16:
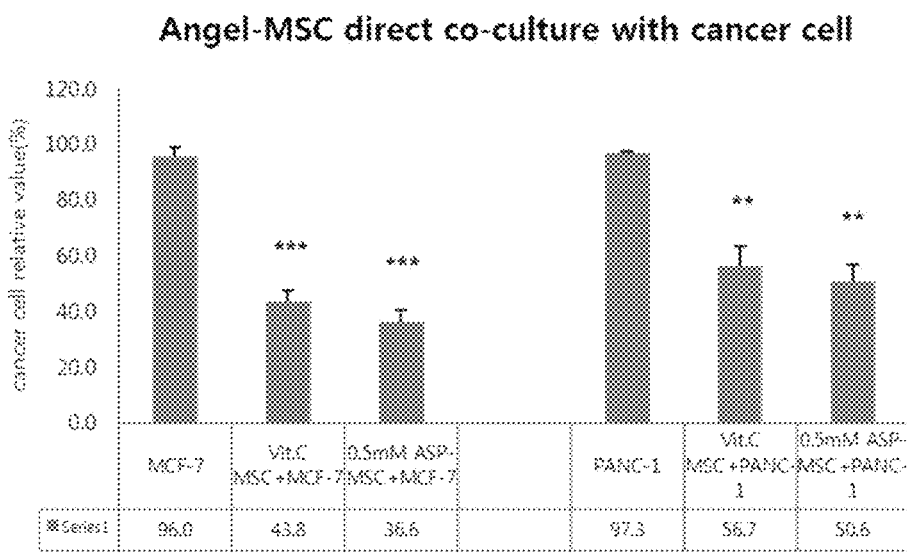
FIG. 16 shows a result of identification of inhibitory activity against proliferation of cancer cells, after direct co-culture of Vit.C-MSC cultured in a 0.5 mM aspirin-containing medium with breast cancer cells (MCF-7) or pancreatic cancer cells (PANC-1) in a cancer cell culture medium.

The MSCs of the control MSC$^+$ cancer cells of FIGS. 14 to 16 were Vit.C-MSCs which were cultured in a medium containing 0.2 mM ascorbic acid to be pre-treated with vitamin C.

6-2: Cancer Stem Cells

The ASP-Vit.C-MSCs, that is, Vit.C-MSCs, treated with aspirin in the same manner as in Example 6-1, were produced and then the anticancer effects of the ASP-Vit.C-MSCs were identified by direct co-culture with cancer stem cells.

The cancer stem cells were labeled with red fluorescent dye, were seeded at $0.5\times10^5$ cells/dish in a 100-mm cell culture dish seeded with $0.5\times10^6$ ASP-Vit.C-MSCs and then directly co-cultured in a $CO_2$ incubator at 37° C. for 48 hours.

After 48 hours, the cancer stem cells were collected, the total cell number, viability and size were measured, the distribution of the cancer stem cells labeled with red fluorescent dye was identified with FACS and anti-cancer activities of Angel-MSCs against cancer stem cells were comparatively analyzed.

Example 7: Identification of Anticancer Effects by Indirect Co-Culture of Vit.C-MSCs Cultured in Aspirin-Containing Medium with Cancer Cells 7-1: Breast Cancer and Pancreatic Cancer Cells In order to conduct indirect co-culture, a transwell allowing for dual cell culture was used. Cancer cells were attached to the bottom of the well, Vit.C-MSCs were attached to an insert membrane in the well, and the cells were co-cultured in DMEM medium containing 10% FBS in the presence of 5% $CO_2$ for 48 hours at 37° C.

First, the Vit.C-MSCs cultured in a medium containing vitamin C of Example 1 were inoculated at a confluence (density) of 10% (0.5×10⁶ cells) with RKCM-N medium in a T75 flask. After 2 days, when the confluence (density) reached 50 to 60%, a RKCM-N medium, that is, a keratinocyte-SFM medium containing 5% FBS, 2 mM NAC, 0.2 mM ascorbic acid, 0.09 mM calcium, 5 ng/ml rEGF, 5 µg/ml insulin and 74 ng/ml hydrocortisone was treated with aspirin at concentrations of 0.1 mM, 0.5 mM and 1 mM, and cultured for 24 hours, and ASP-Vit.C-MSCs (Angel-stem cells) were collected. ASP-Vit.C-MSCs collected for each aspirin concentration were each seeded at 1.4×10⁵ cells/well into an insert transwell (6-well) and placed on an underwell provided with cancer cells.

In order to identify the anticancer effects by indirect co-culture of ASP-Vit.C-MSCs with cancer cells, an insert transwell (6-well) containing ASP-Vit.C-MSCs having each aspirin concentration was placed on a under-well of transwell (6-well), to which the MCF-7 and PANC-1 cancer cells were each attached, the cells were cultured in DMEM medium containing 10% FBS for 48 hours and cancer cells were collected. Cell number, viability and cell size of collected cancer cells were determined with automated cell counter Luna (Logoy).

Figure 17:
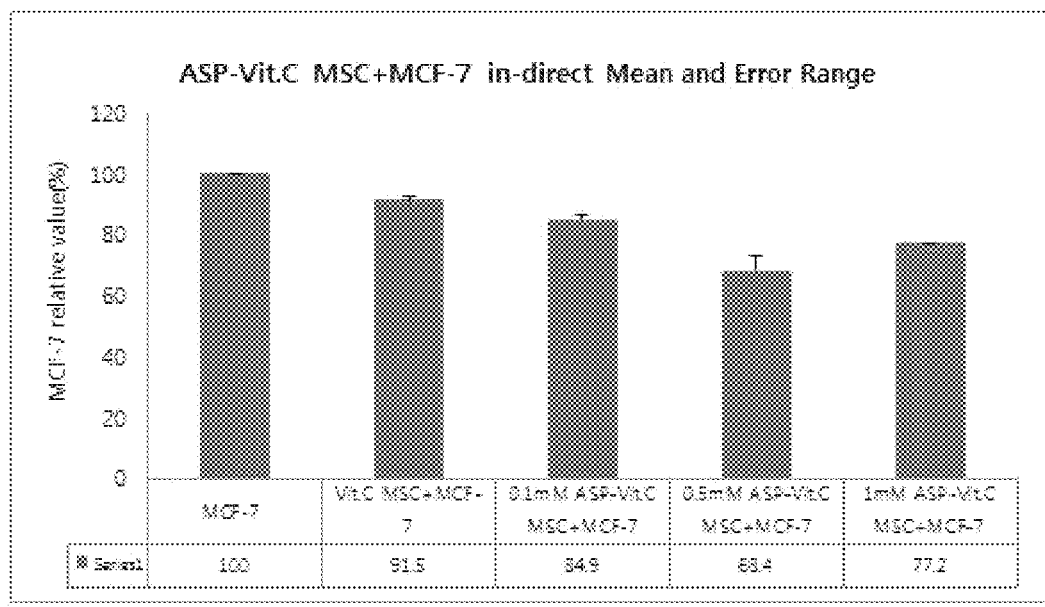
FIG. 17 shows the number of cancer cells, after direct co-culture of Vit.C-MSCs cultured in an aspirin-containing medium with breast cancer cells (MCF-7) in a cancer cell culture medium.
Figure 18:
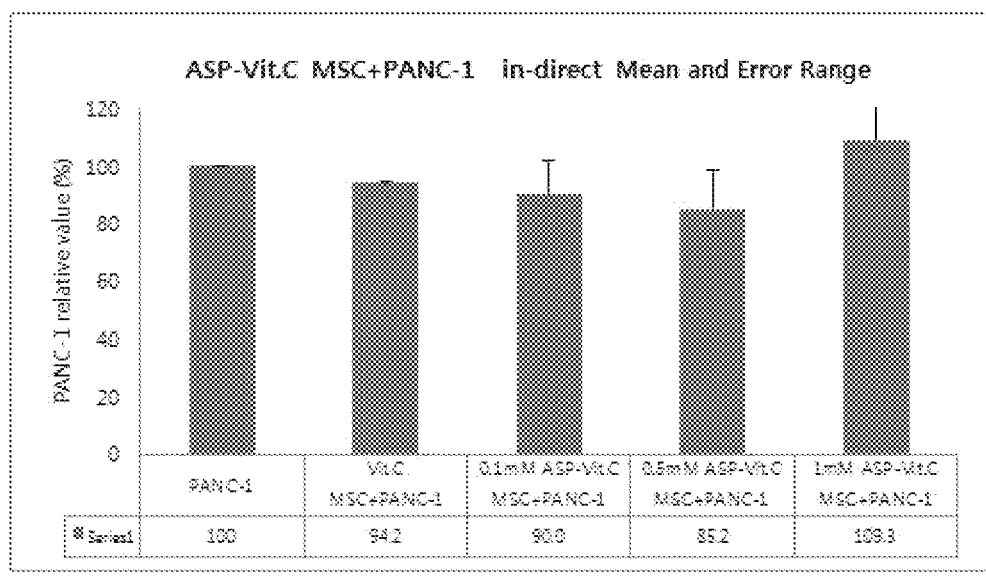
FIG. 18 shows the number of cancer cells, after direct co-culture of Vit.C-MSCs cultured in an aspirin-containing medium with PANC-1 cancer cells in a cancer cell culture medium.
Figure 19:
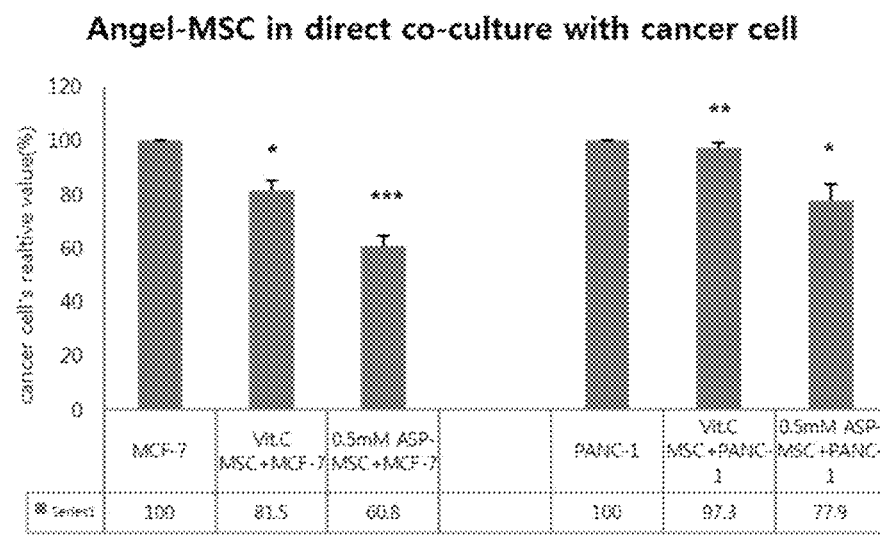
FIG. 19 shows a result of identification of inhibitory activity against proliferation of cancer cells after direct co-culture of Vit.C-MSCs cultured in a 0.5 mM aspirin-containing medium with and breast cancer cells (MCF-7) or pancreatic cancer cells (PANC-1) in a cancer cell culture medium.

As a result, the ASP-Vit.C-MSCs having an aspirin concentration of 0.5 mM exhibited excellent inhibitory activity against proliferation of cancer cells, as compared to Vit.C-MSCs, in both breast cancer cells (MCF-7) and pancreatic cancer cells (PANC-1) (FIGS. 17 to 19). In other words, it was confirmed that Angel stem cells, ASP-Vit.C-MSCs, exhibited superior anticancer effect to Vit.C-MSCs.

The MSCs of the control MSC⁺ cancer cells of FIGS. 17 to 19 were Vit.C-MSCs which were cultured in a medium containing 0.2 mM ascorbic acid to be pre-treated with vitamin C.

7-2: Cancer Stem Cells

The anticancer effect of ASP-Vit.C-MSCs was identified by indirect co-culture of cancer stem cells and Vit.C-MSCs using a transwell allowing for dual cell culture.

First, cancer stem cells cultured in a spherical form having a size of 200 to 400 µm were seeded at 1.4×10⁵ cells in a underwell of the transwell (6-well) and an insert transwell (6-well) seeded at 1.4×10⁵ cells/well with ASP-Vit.C-MSCs was placed on the underwell. The Vit-C-MSCs cultured in a medium containing vitamin C of Example 1 were prepared in the same manner as in Example 7-1.

After indirect co-culture for 48 hours at 37° C. in a CO₂ incubator, the cancer stem cells were collected, and the total cell number, viability and cell size were measured to comparatively analyze the anticancer activities of Angel MSCs against cancer stem cells.

Example 8: Gene Expression Analysis of Vit.C-MSCs Cultured in Aspirin-Containing Medium Vit.C-MSCs cultured in a medium containing vitamin C of Example 1 were cultured for 2 days for adherence and stabilization, and then cultured for 24 hours in a fresh medium supplemented with aspirin at concentrations of 0.1 mM, 0.5 mM and 1 mM. Next, expression of genes relating to anticancer mechanisms, and genes relating to apoptosis and angiogenesis were identified.

The ASP-Vit.C-MSCs cultured in a T75 flask were isolated by treatment with 0.25% trypsin/1 mM EDTA, washed with PBS and then collected by centrifugation at 1,500 rpm for 5 minutes. Total RNA was extracted from the collected cells using TRIzol® Reagent (15596-026, Thermo). cDNA was synthesized from 1 to 3 µg of RNA with DiaStar 2× RT Pre-Mix (Solgent, DR41-P096). In order to cDNA synthesis efficiency, Random hexamers (Invitrogen, increase N8080127) and RiboLock RNase (Thermo Scientific, EO0384) were used in combination. Each reagent was mixed at the concentration according to the manufacturer's instructions and then analyzed using a Tprofessional TRIO Thermocycler (Biometra) at 50° C. to 55° C. for 60 minutes and then at 95° C. for 5 minutes. RT-PCR was carried out by gene amplification using Tprofessional TRIO Thermocycler (Biometra) under conditions of 30 cycle repetition of the process including denaturation of DNA (cDNA) with 25 µl of 2×h-Tag PCR Smart mix (SolGent, STD01-M50h), 2 µl of Primer F (10 pmole/µl, Bioneer) and 2 µl of Primer R (10 pmole/µl, Bioneer) at 98° C. for 10 seconds, heating the primer at each annealing temperature for 30 seconds and elongating the PCR product at 72° C. for 1 minute. The primer sequences for each gene are shown in Table 3.

The PCR product was electrophoresed at 110V using 2.0% agarose gel and 1×TAE reagent for 1 hour and 30 minutes and then imaged with Fuji molecular imaging software. Beta-actin was used as a control gene.

In order to assay gene expression, real-time PCR was performed with THUNDERBIRD SYBR qPCR Mix (TOYOBO QPS-201T). Real-time PCR was conducted using ABapplied Biosystems (StepONE real time PCR system, life technologies) under conditions of 40 cycle repetition of the process including denaturation of DNA with 10 µl of THUNDERBIRD SYBR qPCR Mix, 0.5 µl of 10 µM Primer Fw (Bioneer), 0.5 µl of 10 µM of Primer Rv (Bioneer) and 1 µl of cDNA at 95° C. for 15 seconds and heating the primer at each annealing temperature for 60 seconds.

Real-time PCR was carried out using PikoReal™ real-time PCR (Thermo Fisher Scientific) instrument and Maxima SYBR master mix (×2) (Thermo PIKOREAL 96) (Thermo, #K0221). The PCR cycle was conducted by denaturation at 95° C. for 15 seconds and then annealing and extension at 60° C. for 60 seconds. Such a cycle was performed 40 times in total. Comparison in expression levels was carried out by comparing the gene expression levels through relative comparison using the Ct value of housekeeping genes (b-act) and the Ct value of target genes.

TABLE 3

Table Primers used for qPCR amplification of target genes

| Gene | | Primer sequences 5'→3' |
|---|---|---|
| hTRAIL | FW | ATGGCTATGATGGAGGTCCAGG (SEQ ID NO: 1) |
| | Rv | TCAGCTCGTTGGTAAAGTACACG (SEQ ID NO: 2) |
| h Fas L | FW | CTGGGGATGTTTCAGCTCTT (SEQ ID NO: 3) |
| | Rv | GTGGCCTATTTGCTTCTCCAA (SEQ ID NO: 4) |

TABLE 3-continued

Table Primers used for qPCR amplification of target genes

| Gene | | Primer sequences 5'→3' |
|---|---|---|
| h CXCR4 | FW | GCGGAAAACCAAGACGCTC (SEQ ID NO: 5) |
| | Rv | TTCATGTGCGCGTAACTGTC (SEQ ID NO: 6) |
| h VEGF-A | FW | TGAGCTTCCTACAGCACAAC (SEQ ID NO: 7) |
| | Rv | GAACGCTCCAGGACTTATACC (SEQ ID NO: 8) |
| h Nrf2 | FW | ACCAGTGGATCTGCCAACTA (SEQ ID NO: 9) |
| | Rv | ACGTAGCCGAAGAAACCTCA (SEQ ID NO: 10) |
| h c-Myc | FW | AAGGCCCCCAAGGTAGTTAT (SEQ ID NO: 11) |
| | Rv | TTCCGCAACAAGTCCTCTTC (SEQ ID NO: 12) |
| h p21 | FW | TGTCTTGTACCCTTGTGCCT (SEQ ID NO: 13) |
| | Rv | GCGTTTGGAGTGGTAGAAATC (SEQ ID NO: 14) |
| h Sox 2 | FW | GCGGAAAACCAAGACGCTC (SEQ ID NO: 15) |
| | Rv | TTCATGTGCGCGTAACTGTC (SEQ ID NO: 16) |
| h Nanog | FW | TCCAACATCCRCAACCTCAGC (SEQ ID NO: 17) |
| | Rv | CCTTCTGCGTCACACCATTG (SEQ ID NO: 18) |
| h Oct4 | FW | CACTGTACTCGGTCCCTTTC (SEQ ID NO: 19) |
| | Rv | CAGGCACCTCAGTTTGAATGC (SEQ ID NO: 20) |

Example 9: Analysis of Anticancer-, Apoptosis- and Angiogenesis-Related Genes in Vit.C-MSCs Cultured in Aspirin-Containing Medium 9-1: Identification of Anticancer Mechanisms Through Fas L, TRAIL and CXCR4 Gene Expression Analysis The Vit.C-MSCs cultured in a medium containing vitamin C of Example 1 were cultured for 2 days for adherence and stabilization, and then cultured in a fresh medium supplemented with aspirin at concentrations of 0.1 mM, 0.5 mM and 1 mM for 24 hours.

Since Fas L expressed in stem cells binds to Fas of cancer cells to induce apoptosis of the cancer cells through an apoptosis pathway, expression of Fas L genes involved in apoptosis of the cancer cells could be identified. In addition, DR4/DR5, including such FAS, belongs to FDAA (Fas-associated protein with death domain), which is a receptor involved in the apoptosis pathway, and TRAIL binds to the receptor called "DR4/DR5", to induce apoptosis. Thus, expression of TRAIL genes in addition to Fas L was identified. Real-time PCR (RT-PCR) was carried out in the same manner as in Example 8, and the primers set forth in Table 3 were used.

Figure 21:
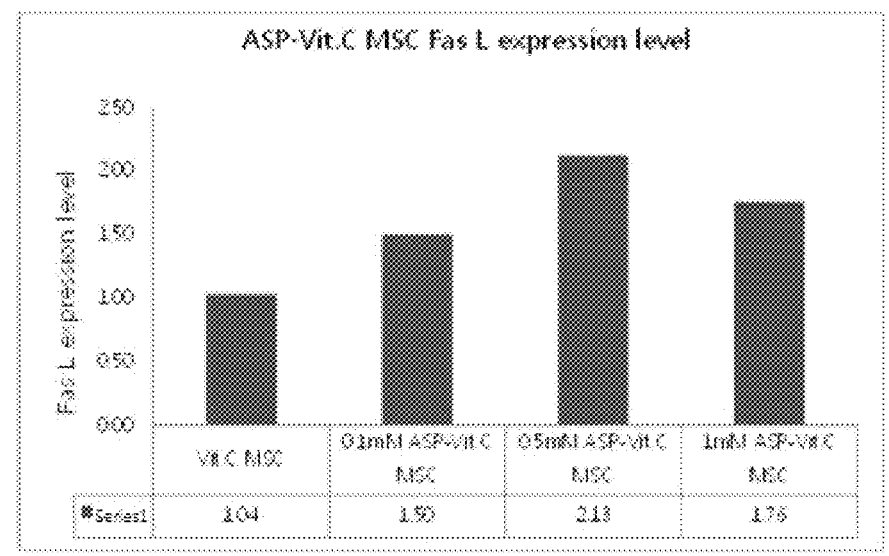
FIG. 21 shows a result of real-time PCR to assay the expression of Fas L in Vit.C-MSCs cultured in media containing aspirin at concentrations of 0.1, 0.5 and 1 mM.
Figure 22:
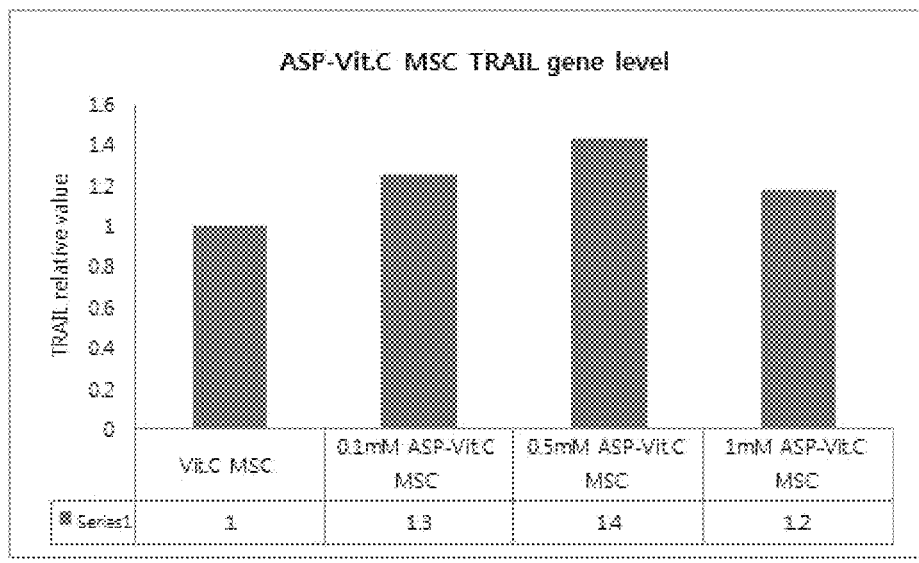
FIG. 22 shows a result of real-time PCR to compare the expression of TRAIL in Vit.C-MSCs cultured in media containing aspirin at concentrations of 0.1, 0.5 and 1 mM.
Figure 23:
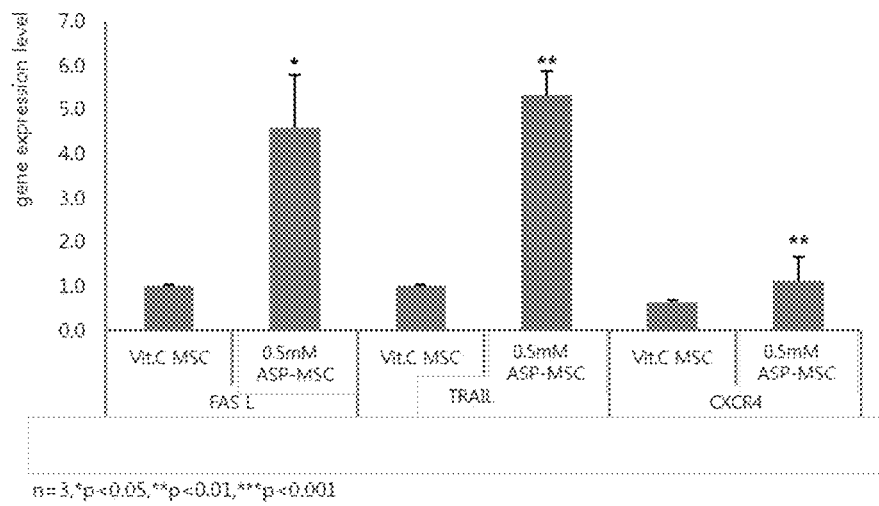
FIG. 23 shows comparison in expression levels of Fas L, TRAIL and CXCR4 in Vit.C-MSCs cultured in a 0.5 mM aspirin-containing medium.

As a result, it could be seen that the expression of Fas L and TRAIL, which are genes associated with anticancer mechanisms involved in apoptosis of cancer cells, was the highest in Vit.C-MSCs cultured in a medium containing aspirin at a concentration of 0.5 mM (FIGS. 21 to 23). That is, it could be seen that the anticancer effect of Angel-stem cells, ASP-Vit.C-MSCs, was the best in 0.5 mM aspirin.

In addition, the expression of CXCR4 genes acting as a homing effector was identified (FIG. 23). As a result, Vit.C-MSCs cultured in an aspirin-containing medium were found to have anticancer activity through pathways associated with Fas L, TRAIL and CXCR4.

9-2: Identification of Angiogenesis of Cancer Cells Through VEGF Gene Expression Analysis The Vit.C-MSCs cultured in a medium containing vitamin C of Example 1 were cultured for 2 days for adherence and stabilization, and then cultured for 24 hours in a fresh medium supplemented with aspirin at concentrations of 0.1 mM, 0.5 mM and 1 mM.

Since VEGF expressed in stem cells is involved in angiogenesis of cancer cells, expression of VEGF genes could be identified. RT-PCR was carried out in the same manner as in Example 8, and the primers set forth in Table 3 were used.

Figure 24:
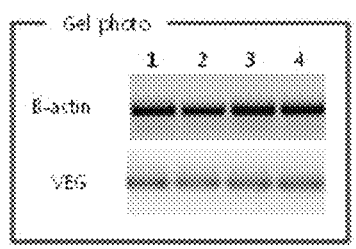
FIG. 24A shows a result of RT-PCR to identify the expression of VEGF in Vit.C-MSCs cultured in media containing aspirin at concentrations of 0.1, 0.5 and 1 mM
FIG. 24B shows comparison in the expression of VEGF after RT-PCR (1: Vit.C MSC, 2: 0.1 mM ASP-Vit.C MSC, 3: 0.5 mM ASP-Vit.C MSC, 4: 1 mM ASP-Vit.C MSC)
Figure 24:
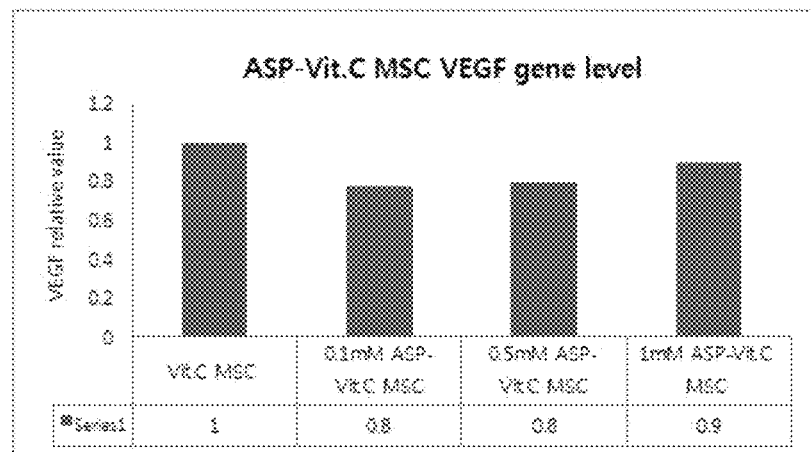

As a result, it could be seen that the expression of VEGF, which is involved in angiogenesis of cancer cells, was the lowest in Vit.C-MSCs cultured in a medium containing aspirin at a concentration of 0.5 mM (FIG. 24). That is, it could be seen that the anticancer effect of Angel-stem cells, ASP-Vit.C-MSCs, was the best in 0.5 mM aspirin.

9-3: Oncogenic Transformation Reduction Effect

Expression levels of Nrf2, c-myc and p21 genes were compared between MSCs and Vit-C-MSCs (Angel-stem cells) cultured in 0.5 mM aspirin-containing medium under the same conditions as in Example 7. RT-PCR was performed in the same manner as in Example 8, and the primers set forth in Table 3 were used.

Figure 25:
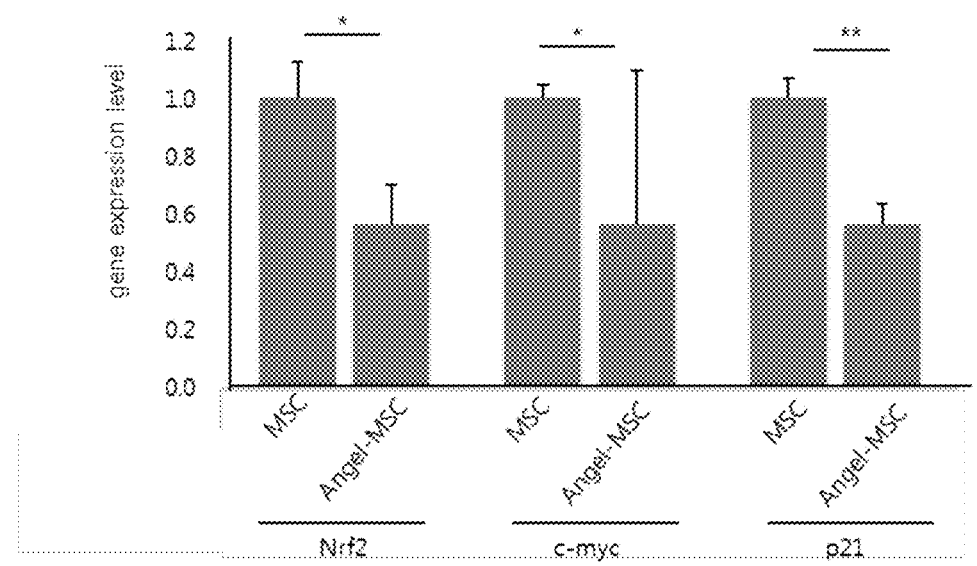
FIG. 25 shows the degree of expression of Nrf2, c-myc and p21 in Vit.C-MSCs cultured in a 0.5 mM aspirin-containing medium.

As a result, as shown in FIG. 25, the expression levels of Nrf2, c-myc and p21 genes were all decreased, which is evidence suggesting that adipose-derived stem cells cultured in the aspirin-containing medium can be free from oncogenic transformation (Juan et al., *Molecular Cancer*, 13: 20, 2014). The decrease in the p21 genes may indicate that stem cells became much younger.

In addition, the expression of Sox2, Oct4 and Nanog was analyzed and compared between Angel-stem cells and MSCs to analyze stem cell characteristics of the Angel-stem cells.

Figure 26:
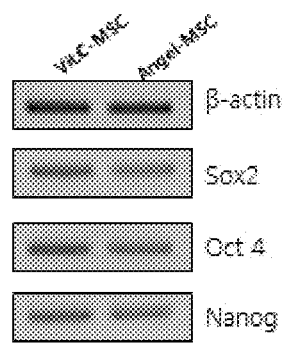
FIG. 26 shows the degree of expression of Sox2, Oct4 and Nanog in Vit.C-MSCs cultured in a 0.5 mM aspirin-containing medium.

As a result, Angel-stem cells were expressed in the same manner as MSCs, and maintained the characteristics of stem cells (FIG. 26).

Example 10: Gene Expression Analysis of Cancer Cells Co-Cultured Indirectly with Vit.C-MSCs Cultured in Aspirin-Containing Medium The Vit-C-MSCs (Angel-stem cells) cultured in an aspirin-containing medium under the same conditions as in Example 7 were indirectly co-cultured with cancer cells and the gene expression in the cancer cells was analyzed. Gene expression analysis was carried out in the same manner as in Example 8.

The primers of respective genes used for gene expression analysis are shown in Tables 3 and 4.

TABLE 4

Table Primers used for qPCR amplification of target genes

| Gene | | Primer sequences 5'→3' |
|---|---|---|
| h Bcl2 | FW | GGGTACGATAACCGGGAGATAGTGA (SEQ ID NO: 21) |
| | Rv | GGAGGAGAAGATGCCCGGTG (SEQ ID NO: 22) |
| h PPAR-γ | FW | TTAGATGACAGCGACTTGGC (SEQ ID NO: 23) |
| | Rv | GGCTTGTAGCAGGTTGTCTT (SEQ ID NO: 24) |
| h Apaf 1 | FW | CTTCTTCCAGTGTAAGGACAGT (SEQ ID NO: 25) |
| | Rv | CAGCCTGCCATTCCATGTAT (SEQ ID NO: 26) |

10-1: Expression of Apoptotic Genes in Cancer Cells

In order to identify the cancer cell proliferation inhibitory mechanism by Vit-C-MSCs (Angel-stem cells) cultured in an aspirin-containing medium, expression of apoptosis-related factors in cancer cells was analyzed.

Figure 27:
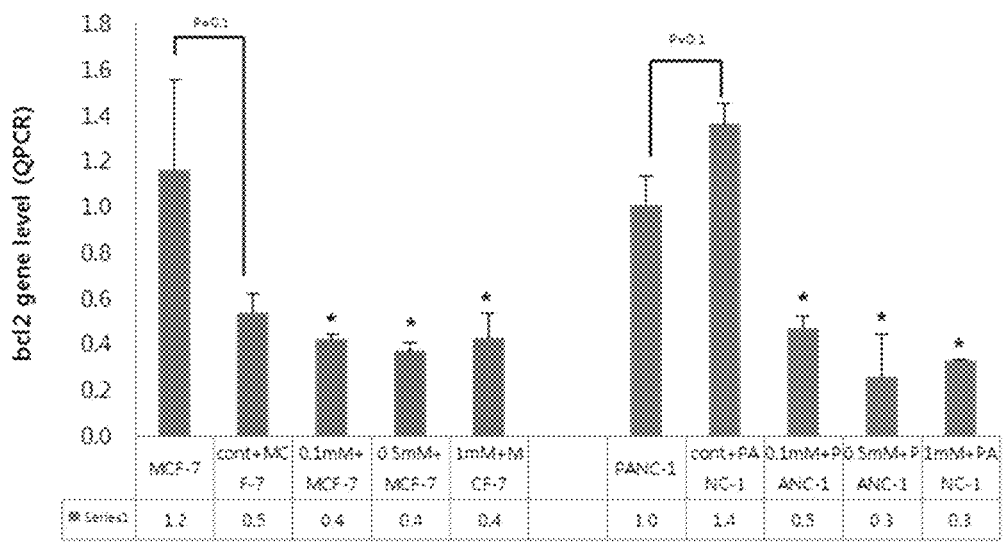
FIG. 27 shows an analysis result of the expression of Bcl-2 genes in cancer cells indirectly co-cultured under cancer cell culture conditions with Vit-C-MSC (Angel-stem cells) cultured in a 0.5 mM aspirin-containing medium.
Figure 28:
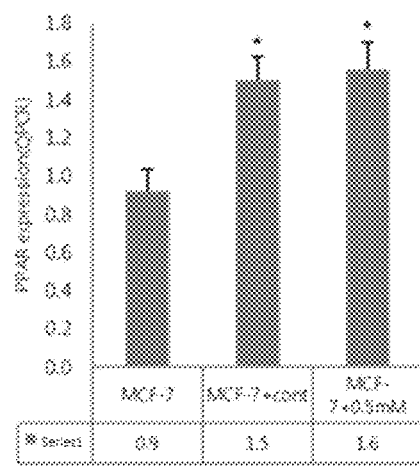
FIG. 28 shows a result of analysis of the expression of PPAR-γ genes in cancer cells indirectly co-cultured under cancer cell culture conditions with Vit-C-MSCs (Angel-stem cells) cultured in an aspirin-containing medium.
Figure 29:
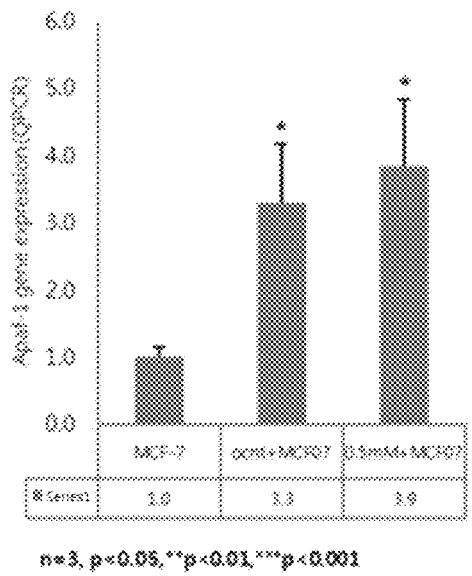
FIG. 29 shows a result of analysis of the expression of Apaf-1 genes in cancer cells indirectly co-cultured under cancer cell culture conditions with Vit-C-MSCs (Angel-stem cells) cultured in an aspirin-containing medium.

As a result, it was confirmed that Bcl-2 expression was decreased in indirectly co-cultured breast cancer and pancreatic cancer cells (FIG. 27). In addition, it was confirmed that the expression of PPAR-γ and Apaf-1 was increased in indirectly co-cultured breast cancer cells (FIGS. 28 and 29). This indicates that co-culture with Vit.C-MSCs (Angel-stem cells) cultured in an aspirin-containing medium promotes apoptosis of the cancer cells.

10-2: Inhibitory Effect of Angel Stem Cells on Cancer Cell Metastasis

In order to identify the inhibitory effect of Vit-C-MSCs (Angel stem cells) cultured in an aspirin-containing medium against metastasis of cancer cells, expression of Oct4 genes in cancer cells was analyzed. The Oct4 primers used for analysis were the same primers as in Example 9-3 (Table 3).

It has been reported that Oct4 is used as an indicator of cancer metastasis (Liu et al., *Ann Surg.* 253 (6): 1165-71, 2011; HAI LIN et al., *MOLECULAR MEDICINE REPORTS* 9: 1335-1342, 2014). Therefore, as expression of Oct4 is decreased, the degree of metastasis is low.

Figure 30:
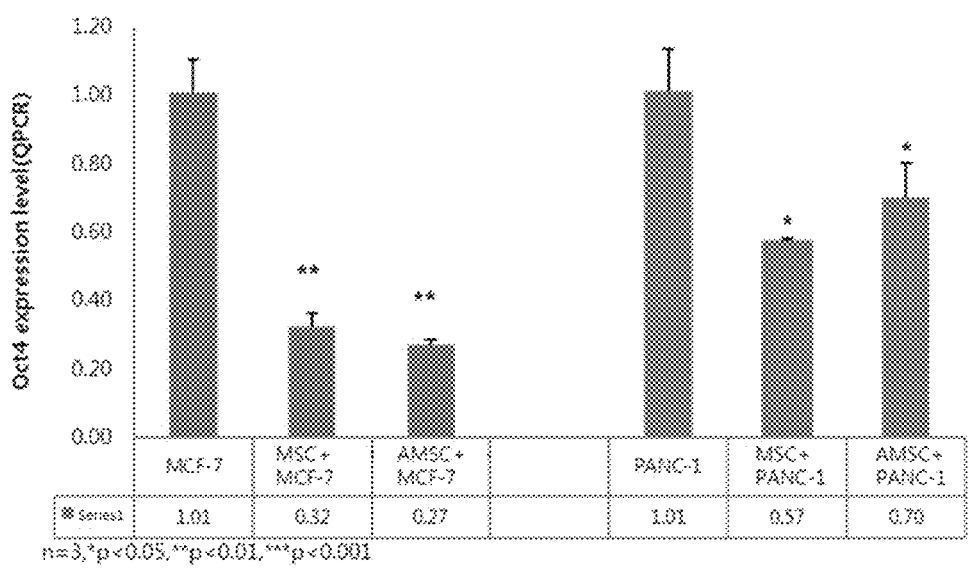
FIG. 30 shows a result of analysis of the expression of Oct4 genes in cancer cells indirectly co-cultured under cancer cell culture conditions with Vit-C-MSCs (Angel-stem cells) cultured in an aspirin-containing medium.

It could be seen from results of FIG. 30 that Oct4 expression in indirectly co-cultured breast and pancreatic cancer cells was decreased.

INDUSTRIAL APPLICABILITY

Since the medium for producing mesenchymal stem cells containing vitamin C and aspirin according to the present invention provides production of mesenchymal stem cells that inhibit proliferation of cancer cells, while maintaining the activity thereof, it is very useful for securing safety of stem cell therapeutic agents from cancers and for producing anticancer cell therapeutic agents.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

It will be deemed that alterations and modifications of the present invention are easily used by those skilled in the art and such alterations and modifications fall within the spirit and scope of the invention.

The invention claimed is:

1. A method for producing mesenchymal stem cells with improved ability to directly inhibit proliferation of cancer cells, the method comprising culturing the mesenchymal stem cells in a medium containing 0.5 mM aspirin and vitamin C,
wherein the mesenchymal stem cells are derived from adipose tissue.

2. The method according to claim 1, wherein the medium is Dulbecco's Modified Eagle Medium (DMEM) containing 5 to 10% Fetal Bovine Serum (FBS) and N-acetyl cysteine (NAC) or Keratinocyte-Serum Free Medium (K-SFM) containing 5 to 10% FBS and NAC.

3. The method according to claim 2, wherein the medium further comprises calcium, recombinant Epidermal Growth Factor (rEGF), insulin and hydrocortisone.

4. The method according to claim 1, wherein the medium is pre-treated with vitamin C.

5. The method according to claim 1, wherein the cancer cells are breast cancer, pancreatic cancer, glioma, gliosarcoma, anaplastic astrocytoma, medulloblastoma, lung cancer, small cell lung cancer, cervical carcinoma, colon cancer, rectal cancer, chordoma, throat cancer, Kaposi's sarcoma, lymphatic sarcoma, lymphatic endothelial sarcoma, colorectal cancer, endometrial cancer, ovarian cancer, leukemia, prostate cancer, kidney cell carcinoma, liver carcinoma, cholangiocarcinoma, choriocarcinoma, seminoma, testicular tumor, Wilm's tumor, Ewing's tumor, bladder carcinoma, angiosarcoma, endothelial sarcoma, adenocarcinoma, hidradenoma, sebaceous carcinoma, papillary carcinoma, papillary sarcoma, cystic sarcoma, bronchial carcinoma, medullary carcinoma, mast cell tumor, mesothelioma, synovioma, melanoma, leiomyoma, rhabdomyoma, neuroblastoma, retinoblastoma, oligodendroglioma, acoustic neuroma, hemangioblastoma, meningioma, pinealoma, ependymoma, craniopharyngioma, epithelial carcinoma, embryonal carcinoma, squamous cell carcinoma, basal cell carcinoma, fibrosarcoma, myxoma, mucosal sarcoma, liposarcoma, chondrosarcoma, osteogenic sarcoma or cancer stem cells.

6. The method according to claim 1, wherein the culture is conducted for 24 hours.

7. The method according to claim 1, wherein the medium contains 0.05 to 1 mM vitamin C.

8. The method according to claim 1, wherein the cancer cells are breast cancer cells.

9. The method of claim 1, wherein the cancer cells are pancreatic cancer cells.

* * * * *

UNITED STATES PATENT AND TRADEMARK OFFICE
CERTIFICATE OF CORRECTION

PATENT NO. : 11,788,061 B2
APPLICATION NO. : 16/321520
DATED : October 17, 2023
INVENTOR(S) : Jeong Chan Ra Page 1 of 1

It is certified that error appears in the above-identified patent and that said Letters Patent is hereby corrected as shown below:

In the Specification

Column 14, Line 11, "2x" should be -- 2X --.

Column 14, Line 24, "2xh-Tag" should be -- 2Xh-Tag --.

Column 14, Line 31, "1xTAE" should be -- 1X TAE --.

Signed and Sealed this
Fourteenth Day of November, 2023

Katherine Kelly Vidal
*Director of the United States Patent and Trademark Office*